US007759388B2

(12) United States Patent
Suzuki et al.

(10) Patent No.: US 7,759,388 B2
(45) Date of Patent: Jul. 20, 2010

(54) PHENYLALANINE DERIVATIVES

(75) Inventors: Nobuyasu Suzuki, Kawasaki (JP);
Toshihiko Yoshimura, Kawasaki (JP);
Hiroyuki Izawa, Kawasaki (JP);
Kazuyuki Sagi, Kawasaki (JP); Shingo Makino, Kawasaki (JP); Eiji Nakanishi, Kawasaki (JP); Masahiro Murata, Kawasaki (JP); Takashi Tsuji, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 12/253,060

(22) Filed: Oct. 16, 2008

(65) Prior Publication Data

US 2009/0048236 A1 Feb. 19, 2009

Related U.S. Application Data

(60) Division of application No. 10/402,006, filed on Mar. 31, 2003, now Pat. No. 7,452,905, which is a continuation of application No. PCT/JP01/08489, filed on Sep. 28, 2001.

(30) Foreign Application Priority Data

Sep. 29, 2000 (JP) .............................. 2000-299490
Feb. 19, 2001 (JP) .............................. 2001-041885

(51) Int. Cl.
*A61K 31/4035* (2006.01)
*C07D 209/48* (2006.01)

(52) U.S. Cl. ..................................... 514/417; 548/479
(58) Field of Classification Search ................. 514/417; 548/479

See application file for complete search history.

(56) References Cited

U.S. PATENT DOCUMENTS

| 6,197,794 B1 | 3/2001 | Head et al. |
| 6,388,084 B1 | 5/2002 | Kaplan et al. |
| 6,610,710 B2 | 8/2003 | Tanaka et al. |
| 7,160,874 B2 | 1/2007 | Tanaka et al. |
| 7,193,108 B2 | 3/2007 | Chiba et al. |
| 2003/0220268 A1 | 11/2003 | Makino et al. |
| 2005/0222141 A1 | 10/2005 | Sagi et al. |
| 2006/0009476 A1 | 1/2006 | Kataoka et al. |
| 2006/0223836 A1 | 10/2006 | Makino et al. |
| 2008/0108634 A1 | 5/2008 | Sagi et al. |

FOREIGN PATENT DOCUMENTS

| WO | WO 98/53814 | 12/1998 |
| WO | WO 99/10312 | 3/1999 |
| WO | WO 99/10313 | 3/1999 |
| WO | WO 99/30312 | 6/1999 |
| WO | WO 99/30313 | 6/1999 |
| WO | WO 99/35163 | 7/1999 |
| WO | WO 99/36393 | 7/1999 |
| WO | WO 99/37618 | 7/1999 |
| WO | WO 00/18759 | 4/2000 |
| WO | WO 01/12183 | 2/2001 |
| WO | WO 01/42215 | 6/2001 |
| WO | WO 02/02556 A2 | 1/2002 |
| WO | WO 02/16329 A1 | 2/2002 |

OTHER PUBLICATIONS

Dorwald et al, Side Reactions n Organic Synthesei, 2005, Wiley, VCH, Weinheim p. IX of Preface.
Zeidler et al, Autoimmunity, 1995, vol. 21, pp. 245-252.
Takeuchi et al, J. Clin. Invest., 1993, vol. 92, pp. 3008-3016.
Wellicome et al, Clin. Exp. Immunol., 1993, vol. 92, pp. 412-418.
Yednock et al, Nature, 1992, vol. 356, pp. 63-65.
Baron et al, J. Exp. Med., 1993, vol. 177, pp. 57-68.
Saito et al, Journal of Clinical Laboratory Analysis, 1993, vol. 7, pp. 180-187.
Abraham et al, J. Clin. Invest., 1994, vol. 93, pp. 776-787.
Sagara et al, Int. Arch. Allergy Immunol., 1997, vol. 112, pp. 287-294.
Onuma, The Journal of Dermatology, 1994, vol. 21, pp. 223-232.
Matsui et al, Acta Otolaryngol., 2000, vol. 120, pp. 761-765.
Ebihara et al, Current Eye Research, 1999, vol. 19, No. 1, pp. 20-25.
Baron et al, J. Clin. Invest., 1994, vol. 93, pp. 1700-1708.
Meisel et al, JACC, 1998, vol. 31, No. 1, pp. 120-125.
Shih et al, Circ. Res., 1999, vol. 84, pp. 345-351.
Lumsden et al, Journal of Vascular Surgery, 1997, vol. 26, No. 1, pp. 87-93.
Mori et al, Blood, 2004, vol. 104, No. 7, pp. 2149-2154.
Isobe et al, The Journal of Immunology, 1994, vol. 153, pp. 5810-5818.
Meyers et al, J. Neuroimmunol, Antisense Drug Discovery, 2005; vol. 160 (1-2): pp. 12-24.
Diamant et al, Clin Exp Allergy, 2005; vol. 35 (8) pp. 1080-1087.
Garmy-Susini et al, J. Clin Invest., 2005; vol. 115(6) pp. 1542-1545.
Vu et al, Transplant Proc., Feb. 2005; vol. 37(1), pp. 162-163.
Podolsky et al, J. Clin. Invest., 1993, vol. 92, pp. 372-380.
Okahara et al, Cancer Reserach, 1994, vol. 54, pp. 3233-3236.
Tilley et al, Bioorganic & Medicinal Chemistry Letters, 2001, vol. 11, pp. 1-4.

*Primary Examiner*—Kamal A Saeed
*Assistant Examiner*—Samantha L Shterengarts
(74) *Attorney, Agent, or Firm*—Oblon, Spivak, McClelland, Maier & Neustadt, L.L.P.

(57) ABSTRACT

Specific phenylalanine derivatives or pharmaceutically acceptable salts thereof have an antagonistic effect on the α 4 integrins and, therefore, are usable as therapeutic agents or preventive agents for diseases in which α 4 integrin-depending adhesion process participates in the pathology, such as inflammatory diseases, rheumatoid arthritis, inflammatory bowel diseases, systemic lupus erythematosus, multiple sclerosis, Sjögren's syndrome, asthma, psoriasis, allergy, diabetes, cardiovascular diseases, arterial sclerosis, restenosis, tumor proliferation, tumor metastasis and transplantation rejection.

26 Claims, No Drawings

PHENYLALANINE DERIVATIVES

BACKGROUND OF THE INVENTION

The present invention relates to new phenylalanine derivatives and the use of the phenylalanine derivatives as medicines. It was reported that α 4 integrins participate in diseases in which α 4 integrin-depending adhesion process participates in the pathology, such as inflammatory diseases, rheumatoid arthritis, inflammatory bowel diseases, systemic lupus erythematosus, multiple sclerosis, Sjögren's syndrome, asthma, psoriasis, allergy, diabetes, cardiovascular diseases, arterial sclerosis, restenosis, tumor proliferation, tumor metastasis and transplantation rejection. The compounds of the present invention having an antagonistic effect on the α 4 integrins are usable as therapeutic agents or preventive agents for the above-described diseases.

In the inflammatory reactions, it is generally understood that when a microorganism invades a tissue or when the tissue is injured, leukocytes play an important role for the exclusion of the microorganism or for the repair of the injured tissue. It is also widely understood that in such cases, leukocytes usually circulating in the blood must pass through the vascular wall and be newly supplied to the injured tissue. It has been elucidated that the infiltration of the leukocytes from the blood vessel into the tissue is carried out by integrin molecules which are a group of heterodimeric proteins expressing on the leukocytes. The integrin molecules are classified into at least 8 subfamilies (β 1 through β 8 subfamilies) depending on the β chains thereof. Known typical subfamilies are β 1 and β 3 subfamilies involved in the adhesion of cell ingredients to the extracellular matrix such as collagen and fibronectin; β 2 subfamily involved in cell-to-cell adhesion in the immune system; and β 7 subfamily which mainly participates in the infiltration of leukocytes into mucosal tissues (Shimizu et al., Adv. Immunol. 72: 325-380, 1999). As for the above-described α 4 integrins, two kinds of molecules thereof are known. They are VLA-4 (very late antigen-4) molecule belonging to the β 1 subfamily and comprising α 4 β 1 chain and LPAM-1 (lymphocyte Peyer's patch HEV adhesion molecule-1) molecule belonging to the β 7 subfamily and comprising α 4 β 7 chain. Usually most of leukocytes circulating in the blood have only a low adhesion affinity for the vascular-endothelium cells and they cannot move out of the blood vessel. However, lymphocytes mainly comprising T cells and B cells are capable of moving out of the blood vessel by a so-called lymphocyte homing phenomenon wherein they move from the blood into the lymphoid tissue through the blood vessel wall and then they return into the blood through the lymphatic vessel under the physiological conditions. It is known that LPAM-1 molecules participate in the lymphocyte homing into the lymphoid tissue of an intestinal tract such as Peyer's patch (Butcher et al., Adv. Immunol. 72: 209-253, 1999). On the other hand, when an inflammation occurs, the vascular-endothelium cells are activated by cytokine and chemokine released from the inflamed tissue, the expression of a group of cell surface antigens (adhesion molecules) participating in the adhesion of leukocytes to the vascular-endothelium cells is caused, and a lot of leukocytes infiltrate out of the blood vessel toward the inflamed tissue through the adhesion molecules.

As the cell surface antigens on the vascular-endothelium cells participating in the adhesion of the leukocytes, there have been known E-selectin (adhesion molecule mainly participating in the adhesion of neutrophils), ICAM-1 and VCAM-1 mainly participating in the adhesion of lymphocytes, and MAdCAM-1 mainly participating in the adhesion of lymphocytes in the lymphoid tissue of an intestinal tract such as Peyer's patch (Shimizu et al., Adv. Immunol. 72: 325-380, 1999). It was reported that in those adhesion molecules, VCAM-1 acts as a ligand of both VLA-4 and LPAM-1 and that MAdCAM-1 acts as the ligand of LPAM-1. As a ligand of both VLA-4 and LPAM-1, fibronectin which is a kind of extracellular matrix is also known (Shimizu et al., Adv. Immunol. 72: 325-380, 1999). The β 1 integrin subfamily to which VLA-4 belongs comprises at least 6 integrins (VLA-1 to VLA-6) using extracellular matrixes such as fibronectin, collagen and laminin as the ligands. Many of integrins using extracellular matrixes as the ligands, such as VLA-5, β 3 subfamily and β 5 subfamily, recognize arginine—glycine—aspartic acid (RGD) sequence in fibronectin, vitronectin, tenascin and osteopontin. On the other hand, in the interaction of VLA-4 and fibronectin, the RGD sequence does not participate but a CS-1 peptide segment comprising leucine—aspartic acid—valine (LDV) as the core sequence participates (Pulido et al., J. Biol. Chem. 266: 10241-10245, 1991). Clements et al. found a sequence similar to LDV in amino acid sequences of VCAM-1 and MAdCAM-1. It has been elucidated that a variant obtained by partially modifying the CS-1-like sequence of VCAM-1 and MAdCAM-1 molecules cannot interact to VLA-4 or LPAM-1 (Clements et al., J. Cell Sci. 107: 2127-2135, 1994, Vonderheide et al., J. Cell. Biol. 125: 215-222, 1994, Renz et al., J. Cell. Biol. 125: 1395-1406, 1994, and Kilger et al., Int. Immunol. 9: 219-226, 1997). Thus, it was found that the CS-1-like sequence is important for the interaction of VLA-4/LPAM-1 and VCAM-1/MAdCAM-1.

It was also reported that the cyclic peptide having the CS-1-like structure is antagonistic both to the interaction of VLA-4 or LPAM-1 with VCAM-1, MAdCAM-1 or CS-1 peptide (Vanderslice et al., J. Immunol. 158: 1710-1718, 1997). The above-described facts indicate that all the interactions of α 4 integrin and VCAM-1, MAdCAM-1 or fibronectin can be blocked by using a suitable α 4 integrin antagonist (the term "α 4 integrin antagonist" in the specification indicates a substance antagonistic to α 4 β 1 and/or α 4 β 7 integrin).

It is also known that the expression of VCAM-1 in vascular-endothelium cells is caused by inflammatory factors such as LPS, TNF-α or IL-1 and that when the inflammation occurs, the infiltration of the leukocytes from the blood vessel into the tissue is carried out by the VLA-4/VCAM-1 adhesion mechanism (Elices, Cell 60: 577-584, 1990, Osborn et al., Cell 59: 1203-1211, 1989 and Issekutz et al., J. Eex. Med. 183: 2175-2184, 1996). Because VLA-4 is expressed on the surfaces of activated lymphocytes, monocytes, eosinophils, mast cells and neutrophils, the adhesion mechanism of VLA-4/VCAM-1 plays an important role for the infiltration of those cells into the inflamed tissue. It was reported that VLA-4 is expressed on various sarcoma cells such as melanoma cells, and it was also elucidated that the adhesion mechanism of VLA-4/VCAM-1 participates in the metastasis of these tumors. By investigating the expression of VCAM-1 in various pathological tissues, it was made apparent that the adhesion mechanism of this VLA-4/VCAM-1 participates in various pathological stages. Namely, it was reported that in addition to the activated vascular-endothelium cells, the expression of VCAM-1 is increased in the inflamed tissues in the patients with autoimmune diseases such as rheumatoid synovial membrane (van Dinther-Janssen, J. Immunol. 147: 4207-4210, 1991 and Morales-Ducret et al., J. Immunol. 149: 1424-1431, 1992), lungs and respiratory tract epithelium in asthma (ten Hacken et al., Clin. Exp. Allergy 12: 1518-1525, 1998) and allergic diseases (Randolph et al., J. Clin. Invest. 104: 1021-1029, 1999), systemic lupus erythematosus (Takeuchi et al., J. Clin. Invest. 92: 3008-3016, 1993), Sjögren's syndrome (Edwards et al., Ann. Rheum. Dis. 52: 806-811, 1993), multiple sclerosis (Steffen et al., Am. J. Pathol. 145: 189-201, 1994) and psoriasis (Groves et al., J. Am. Acad. Dermatol. 29: 67-72, 1993); atherosclerotic plagues (O'Brien et al., J. Clin. Invest. 92: 945-951, 1993), intestinal tissues of the patients with inflammatory bowel diseases such as Crohn's disease and ulcerative colitis (Koizumi et al., Gastroenterol. 103: 840-847, 1992 and Nakamura et al., Lab. Invest. 69: 77-85, 1993), inflamed tissue of Langerhans island of patients with diabetes (Martin et al., J. Autoimmun. 9: 637-643, 1996) and implants during the rejection of transplantation of heart or kidney (Herskowitz et al. Am. J. Pathol. 145: 1082-1094, 1994 and Hill et al., Kidney Int. 47: 1383-1391, 1995). The adhesion mechanism of VLA-4/VCAM-1 participates in these various diseases.

There are many reports showing that in vivo administration of VLA-4 or VCAM-1 antibody was effective in improving the diseases of animal models with those inflammatory diseases. Concretely, Yednock et al. and Baron et al. reported that the in vivo administration of an antibody against α 4 integrins was effective in controlling the incidence rate or in controlling encephalomyelitis in the experimental autoimmune encephalomyelitis models, i.e. multiple sclerosis models (Yednock et al., Nature 356: 63-66, 1992 and Baron et al., J. Exp. Med. 177: 57-68, 1993). Zeidler et al. reported that in vivo administration of an antibody against α 4-integrin was effective in controlling the incidence rate of mouse collagen arthritis (rheumatoid models) (Zeidler et al., Autoimmunity 21: 245-252, 1995). The therapeutic effect of an antibody against α 4-integrin in asthma models was reported by Abraham et al. and Sagara et al. (Abraham et al., J. Clin. Invest. 93: 776-787, 1994 and Sagara et al., Int. Arch. Allergy Immunol. 112: 287-294, 1997). The effect of an antibody against α 4-integrin in inflammatory bowel disease models was reported by Podolsky et al. (Podolsky et al., J. Clin. Invest. 92: 372-380, 1993). The effect of an antibody against α 4-integrin and that against VCAM antibody in insulin-dependent diabetes models were reported by Baron et al. (Baron et al., J. Clin. Invest. 93: 1700-1708, 1994). It was made apparent with baboon models that the restenosis of a blood vessel after an angioplasty carried out because of arteriosclerosis can be inhibited by the administration of α 4 integrin antibody (Lumsden et al., J. Vasc. Surg. 26: 87-93, 1997). It was also reported that α 4 integrin or VCAM antibody is effective in inhibiting the rejection of an implant or inhibiting metastasis of a cancer (Isobe et al., J. Immunol. 153: 5810-5818, 1994 and Okahara et al., Cancer Res. 54: 3233-3236, 1994).

As described above, unlike VCAM-1, MAdCAM-1 which is a ligand of LPAM-1 is constitutively expressed on high endothelial venules (HEV) in the intestinal mucosa, mesenteric lymphatic nodes, Peyer's patch and spleen and it participates in the homing of mucosal lymphocytes. It is also known that LPAM-1/MAdCAM-1 adhesion mechanism not only has physiological roles in the homing of the lymphocytes but also participates in some pathological processes. Briskin et al reported an increase in the expression of MAdCAM-1 in inflamed regions in intestinal tracts of patients with inflammatory bowel diseases such as Crohn's disease and ulcerative colitis (Briskin et al., Am. J. Pathol. 151: 97-110, 1997). Hanninen et al. reported that induction of the expression is observed in an inflamed tissue of Langerhans island of NOD mouse which is a model of an insulin-dependent diabetes (Hanninen et al., J. Immunol. 160: 6018-6025, 1998). The fact that LPAM-1/MAdCAM-1 adhesion mechanism participates in the progress of diseases is apparent from the fact that conditions of mouse models with inflammatory bowel disease (Picarella et al., J. Immunol. 158: 2099-2106, 1997) and the above-described NOD mouse models are improved by the in vivo administration of antibody to MAdCAM or antibody to β 7 integrin (Hanninen et al., J. Immunol. 160: 6018-6025, 1998 and Yang et al., Diabetes 46: 1542-1547, 1997).

The above-described facts indicate the possibility in that employing the blocking of VLA-4/VCAM-1, LPAM-1/VCAM-1 or LPAM-1/MAdCAM-1 adhesion mechanism by a suitable antagonist is effective in treating the chronic inflammatory diseases described above. The use of the antibody against VLA-4 as the VLA-4 antagonist is described in WO 93/13798, WO 93/15764, WO 94/16094 and WO 95/19790. Peptide compounds as VLA-4 antagonists are described in WO 94/15958, WO 95/15973, WO 96/00581 and WO 96/06108. Amino acid derivatives usable as VLA-4 antagonists are described in WO 99/10312, WO 99/10313, WO 99/36393, WO 99/37618 and WO 99/43642. However, none of them is practically used for the therapeutic treatment at present because of the lack of oral bioavailability and immunogenic properties during the use of them for a long period of time.

DISCLOSURE OF THE INVENTION

An object of the present invention is to provide new compounds having α 4 integrin antagonistic effect.

Another object of the present invention is to provide α 4 integrin antagonists.

A further object of the present invention is to provide a pharmaceutical composition containing such new compounds.

An additional object of the present invention is to provide therapeutic agents or preventive agents for diseases in which α 4 integrin-depending adhesion process participates in the pathology, such as inflammatory diseases, rheumatoid arthritis, inflammatory bowel diseases, systemic lupus erythematosus, multiple sclerosis, Sjögren's syndrome, asthma, psoriasis, allergy, diabetes, cardiovascular diseases, arterial sclerosis, restenosis, tumor proliferation, tumor metastasis and transplantation rejection.

For the purpose of solving the above-described problems, the inventors have synthesized various phenylalanine derivatives and examined α 4 integrin antagonistic activities thereof, and the inventors have found that specified, new phenylalanine derivatives have an excellent α 4 integrin antagonistic activity. The present invention has been completed on the basis of this finding.

Namely, the present invention provides phenylalanine derivatives of the following general formula (1) or pharmaceutically acceptable salts thereof:

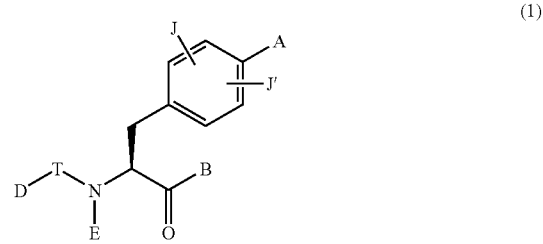

(1)

wherein A represents the following general formula (2-1), (2-2) or (2-3):

(2-1)

-continued

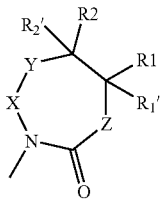
(2-2)

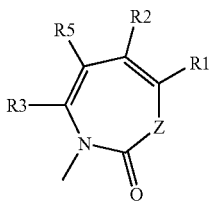
(2-3)

wherein X represents C(=O) or C(—R3)(—R4),

Y represents an interatomic bond, C(—R5)(—R6), C(—R7)=C(—R8) or a lower alkyl chain which may contain one or two of oxygen atoms, sulfur atoms and aromatic rings, Z represents an interatomic bond, C(—R9)(—R10), C(—R11)(—R12)-C(—R13)(—R14), a lower alkyl chain which may contain one or two of oxygen atoms, sulfur atoms and aromatic rings, or an alkylene chain having 2 or 3 carbon atoms, which may contain one or two of oxygen atoms, sulfur atoms or aromatic rings in the chain thereof, each of R1 to R14, R1' and R2' represents a hydrogen atom, a lower alkyl group which may contain a hetero atom(s) in the chain thereof, a lower alkenyl group which may contain a hetero atom(s) in the chain thereof, a lower alkynyl group which may contain a hetero atom(s) in the chain thereof, a cycloalkyl group which may contain a hetero atom(s) in the ring thereof, an aryl group, a heteroaryl group, a lower alkyl group substituted with a cycloalkyl group(s) which may contain a hetero atom(s) in the ring thereof, a lower alkyl group substituted with an aryl group(s), a lower alkyl group substituted with a heteroaryl group(s), a lower alkoxyl group, a lower alkoxyl group substituted with a cycloalkyl group(s) which may contain a hetero atom(s) in the ring thereof, a lower alkoxycarbonyl group, a lower alkylcarbonyl group, a cyano group, a nitro group, a lower alkylsulfonyl group or a lower alkylsulfonylamino group, R1 and R2 may be bonded together to form a saturated or unsaturated ring with C—C on the ring represented by the general formula (2-1) or (2-3), R7 and R8 may be bonded together to form a saturated or unsaturated ring with C—C on the ring represented by the general formula (2-1), R2 and R5 may be bonded together to form a saturated or unsaturated ring with C—C on the ring represented by the general formula (2-1), each set of R1 and R1', R2 and R2', R1' and R2' and R7 and R8 may be bonded together to form a saturated or unsaturated ring with C—C on the ring represented by the general formula (2-2), R2 and R5 or R2' and R5 may be bonded together to form a saturated or unsaturated ring with C—C on the ring represented by the general formula (2-2), the ring formed as described above may have one substituent or more substituents which may be the same or different from each other, and the substituent thereof represents a halogen atom, a hydroxyl group, a lower alkyl group which may contain a hetero atom(s) in the chain thereof, a lower alkenyl group which may contain a hetero atom(s) in the chain thereof, a lower alkynyl group which may contain a hetero atom(s) in the chain thereof, a cycloalkyl group which may contain a hetero atom(s) in the ring thereof, an aryl group, a heteroaryl group, a lower alkyl group substituted with a cycloalkyl group(s) which may contain a hetero atom(s) in the ring thereof, a lower alkyl group substituted with an aryl group(s), a lower alkyl group substituted with a heteroaryl group(s), a lower alkoxyl group, a lower alkoxyl group substituted with a cycloalkyl group(s) which may contain a hetero atom(s) in the ring thereof, a lower alkoxyl group substituted with an aryl group(s), a lower alkoxyl group substituted with a heteroaryl group(s), a cycloalkyloxy group which may contain a hetero atom(s) in the ring thereof, an aryloxy group, a heteroaryloxy group, a lower hydroxyalkyl group, a lower hydroxyalkenyl group, a lower hydroxylalkoxyl group, a lower halogenoalkyl group, a lower halogenoalkoxyl group, a lower halogenoalkenyl group, nitro group, cyano group, a substituted or unsubstituted amino group, carboxyl group, a lower alkyloxycarbonyl group, a substituted or unsubstituted carbamoyl group, a lower alkanoyl group, an aroyl group, a lower alkylthio group, a lower alkylsulfonyl group, a substituted or unsubstituted sulfonylamino group or a substituted or unsubstituted sulfamoyl group, and the substituents may form a ring between them, B represents a hydroxyl group, a lower alkoxyl group or hydroxylamino group, E represents a hydrogen atom, a lower alkyl group, a lower alkenyl group, a lower alkynyl group, a lower alkyl group substituted with a cycloalkyl group(s) which may contain a hetero atom(s) in the ring thereof, a lower alkyl group substituted with an aryl group(s) or a lower alkyl group substituted with a heteroaryl group(s), D represents a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group(s) which may contain a hetero atom(s) in the ring thereof, a lower alkyl group substituted with an aryl group(s), a lower alkyl group substituted with a heteroaryl group(s), a lower alkoxyl group, a lower alkoxyl group substituted with a cycloalkyl group(s) which may contain a hetero atom(s) in the ring thereof, a lower alkoxyl group substituted with an aryl group(s), a lower alkoxyl group substituted with a heteroaryl group(s), a cycloalkyloxy group which may contain a hetero atom(s) in the ring thereof, an aryloxy group, a heteroaryloxy group, a lower hydroxyalkyl group, a lower hydroxyalkenyl group, a lower hydroxyalkoxyl group, a lower halogenoalkyl group, a lower halogenoalkoxyl group, a lower halogenoalkenyl group, nitro group, cyano group, a substituted or unsubstituted amino group, carboxyl group, a lower alkyloxycarbonyl group, a substituted or unsubstituted carbamoyl group, a lower alkanoyl group, an aroyl group, a lower alkylthio group, a lower alkylsulfonyl group, a substituted or unsubstituted sulfonylamino group or a substituted or unsubstituted sulfamoyl group, E and D may be bonded together to form a ring which may contain one or two oxygen, nitrogen or sulfur atoms, T represents an interatomic bond, C(=O), C(=S), S(=O), S(=O)$_2$, NH—C(=O), NH—C(=S), CH$_2$—C(=O) or CH=CH—C(=O), J and J' may be the same or different from each other and each represents a hydrogen atom, a halogen atom, a lower alkyl group, a lower alkyloxy group or nitro group, with the exception of the compounds of the following general formulae (3) and (4-1) to (4-5).

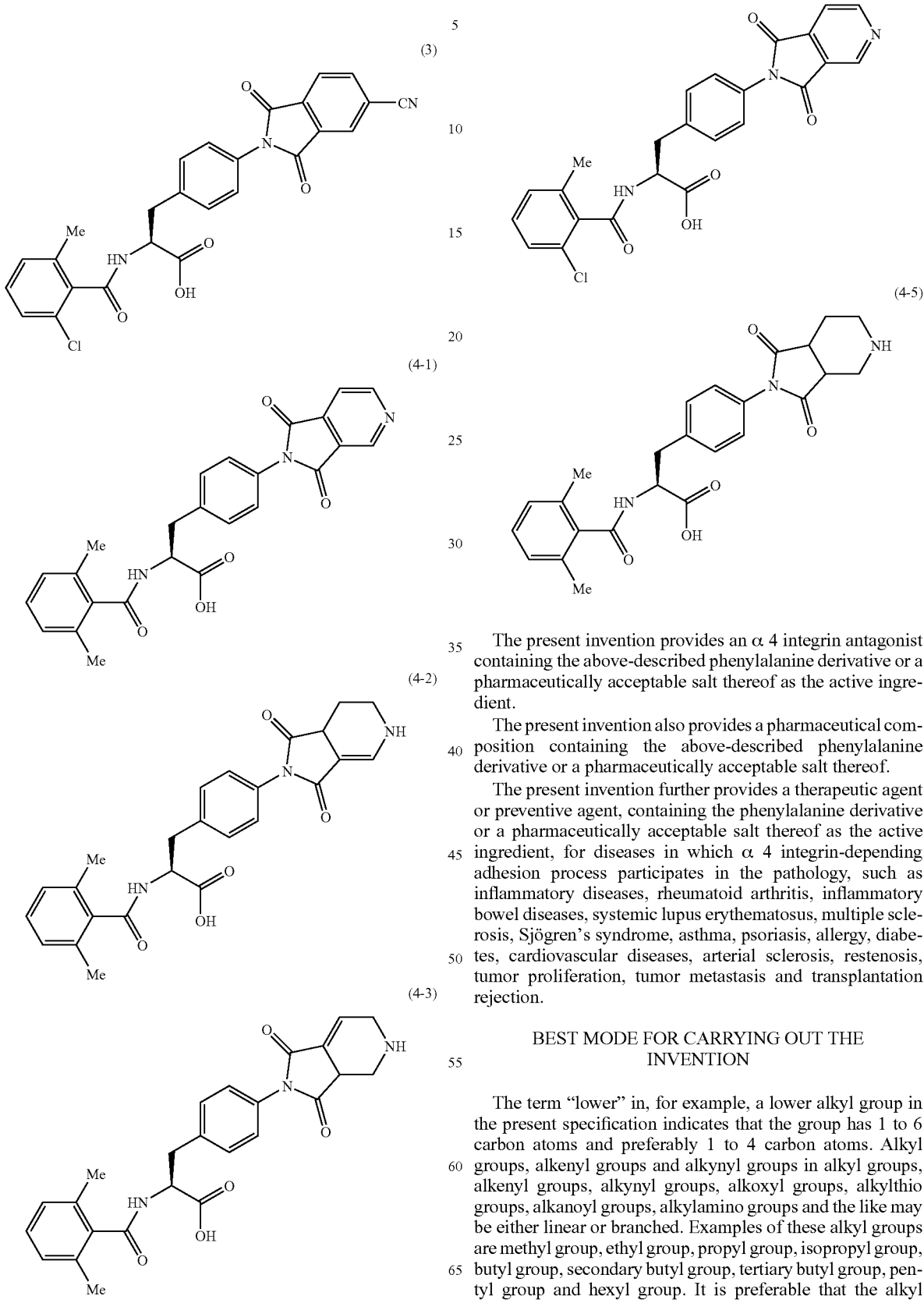

The present invention provides an α 4 integrin antagonist containing the above-described phenylalanine derivative or a pharmaceutically acceptable salt thereof as the active ingredient.

The present invention also provides a pharmaceutical composition containing the above-described phenylalanine derivative or a pharmaceutically acceptable salt thereof.

The present invention further provides a therapeutic agent or preventive agent, containing the phenylalanine derivative or a pharmaceutically acceptable salt thereof as the active ingredient, for diseases in which α 4 integrin-depending adhesion process participates in the pathology, such as inflammatory diseases, rheumatoid arthritis, inflammatory bowel diseases, systemic lupus erythematosus, multiple sclerosis, Sjögren's syndrome, asthma, psoriasis, allergy, diabetes, cardiovascular diseases, arterial sclerosis, restenosis, tumor proliferation, tumor metastasis and transplantation rejection.

BEST MODE FOR CARRYING OUT THE INVENTION

The term "lower" in, for example, a lower alkyl group in the present specification indicates that the group has 1 to 6 carbon atoms and preferably 1 to 4 carbon atoms. Alkyl groups, alkenyl groups and alkynyl groups in alkyl groups, alkenyl groups, alkynyl groups, alkoxyl groups, alkylthio groups, alkanoyl groups, alkylamino groups and the like may be either linear or branched. Examples of these alkyl groups are methyl group, ethyl group, propyl group, isopropyl group, butyl group, secondary butyl group, tertiary butyl group, pentyl group and hexyl group. It is preferable that the alkyl groups have 1 to 6 carbon atoms and more preferable that the groups have 1 to 4 carbon atoms. The alkenyl groups are, for example, vinyl group, propenyl group, butenyl group and pentenyl group. It is preferable that the alkenyl groups have 2 to 6 carbon atoms and more preferable that the groups have 2 to 4 carbon atoms. The alkynyl groups include ethynyl group, propynyl group and butynyl group. It is preferable that the alkynyl groups have 2 to 8 carbon atoms and more preferable that the groups have 2 to 4 carbon atoms. The cycloalkyl groups indicate substituted or unsubstituted cycloalkyl groups such as cyclopropyl group, cyclobutyl group, cyclopentyl group, cyclohexyl group, norbornyl group, adamantyl group and cyclohexenyl group. It is preferable that the cycloalkyl groups have 3 to 8 carbon atoms and more preferable that the groups have 3 to 5 carbon atoms. The alkoxyl groups include methoxyl group, ethoxyl group, propyloxy group, isopropyloxy group, etc. It is preferable that the alkoxyl groups have 1 to 6 carbon atoms and more preferable that the groups have 1 to 4 carbon atoms. The hetero atoms include nitrogen, oxygen, sulfur, etc. The halogen atoms are fluorine, chlorine, bromine and iodine. The halogenoalkyl groups include chloromethyl group, trichloromethyl group, trifluoromethyl group, trifluoroethyl group, pentafluoromethyl group, etc. The halogenoalkoxyl groups include trichloromethoxyl group, trifluoromethoxyl group, etc. The hydroxyalkyl groups include hydroxymethyl group, hydroxyethyl group, etc. The cycloalkyl groups which may contain a hetero atom(s) in the ring thereof may be either substituted or unsubstituted. Their examples include cyclopentyl group, cyclohexyl group, piperidyl group, piperazinyl group, morpholinyl group, pyrrolidinyl group, tetrahydrofuranyl group and uracil group, which are 4-to-8-membered ring, preferably, 5-to-7-membered ring.

In the present specification, the aryl groups are both substituted and unsubstituted aryl groups such as phenyl group, 1-naphthyl group and 2-naphthyl group. They are preferably phenyl group and substituted phenyl group, and the substituents are particularly preferably halogen atoms, alkoxyl groups, alkyl groups, hydroxyl group, halogenoalkyl groups and halogenoalkoxyl groups. The heteroaryl groups are both substituted and unsubstituted heteroaryl groups such as pyridyl group, pyrazyl group, pyrimidinyl group, pyrazolyl group, pyrrolyl group, triazyl group, furyl group, thienyl group, isoxazolyl group, isothiazolyl group, indolyl group, quinolyl group, isoquinolyl group and benzimidazolyl group. Preferred heteroaryl groups are pyridyl group, pyrazyl group, pyrimidinyl group, furyl group, thienyl group and substituted pyridyl, furyl and thienyl groups. Particularly preferred substituents are halogen atoms, alkoxyl groups, alkyl groups, hydroxyl group, halogenoalkyl groups and halogenoalkoxyl groups. The lower alkyl groups substituted with an aryl group(s) include, for example, substituted or unsubstituted benzyl groups and substituted or unsubstituted phenethyl groups. Particularly preferred substituents are halogen atoms, alkoxyl groups, alkyl groups, hydroxyl group, halogenoalkyl groups and halogenoalkoxyl groups. The lower alkyl groups substituted with a heteroaryl group(s) include, for example, pyridylmethyl group, and particularly preferred substituents thereof are halogen atoms, alkoxyl groups, alkyl groups, hydroxyl group, halogenoalkyl groups and halogenoalkoxyl groups. The alkanoyl groups include, for example, formyl groups, acetyl groups, propanoyl group, butanoyl group and pivaloyl group. The aroyl groups include, for example, substituted or unsubstituted benzoyl group and pyridylcarbonyl group, and the substituents thereof are particularly preferably halogen atoms, alkoxyl groups, alkyl groups, hydroxyl group, halogenoalkyl groups and halogenoalkoxyl groups. The halogenoalkanoyl groups include, for example, trichloroacetyl group and trifluoroacetyl group. The alkylsulfonyl groups include, for example, methanesulfonyl group, ethanesulfonyl group, etc. The arylsulfonyl groups include, for example, benzenesulfonyl group and p-toluenesulfonyl group. The heteroarylsulfonyl groups include, for example, pyridylsulfonyl group. The halogenoalkylsulfonyl groups include, for example, trifluoromethanesulfonyl group. The alkyloxycarbonyl groups include, for example, methoxycarbonyl group, ethoxycarbonyl group and tert-butoxycarbonyl group. The aryl-substituted alkoxycarbonyl groups include, for example, benzyloxycarbonyl group and 9-fluorenylmethoxycarbonyl group. The substituted carbamoyl groups include, for example, methylcarbamoyl group, phenylcarbamoyl group and substituted phenylcarbamoyl group, and the substituents thereof are particularly preferably halogen atoms, alkoxyl groups, alkyl groups, hydroxyl group, halogenoalkyl groups and halogenoalkoxyl groups. The substituted thiocarbamoyl groups include, for example, methylthiocarbamoyl group, phenylthiocarbamoyl group and substituted phenylthiocarbamoyl groups, and the substituents thereof are particularly preferably halogen atoms, alkoxyl groups, alkyl groups, hydroxyl group, halogenoalkyl groups and halogenoalkoxyl groups. The substituents of the substituted amino groups in the present specification include lower alkyl groups, lower alkyl groups substituted with an aryl group, lower alkyl groups substituted with a heteroaryl group, lower alkanoyl groups, aroyl groups, lower halogenoalkanoyl groups, lower alkylsulfonyl groups, arylsulfonyl groups, heteroarylsulfonyl groups, halogenoalkylsulfonyl groups, lower alkyloxycarbonyl groups, aryl-substituted lower alkyloxycarbonyl groups, substituted or unsubstituted carbamoyl groups and substituted or unsubstituted thiocarbamoyl groups.

In the above-described general formula (1),
it is preferable that the group indicated as A is the general formula (2-1), the number of the substituents on the ring formed by bond between R1 and R2 or between R7 and R8 is preferably 4 or less and particularly the following general formulae (5-1), (5-2) and (6) are preferable:

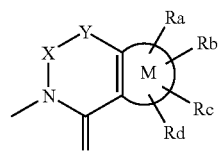

(5-1)

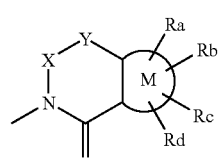

(5-2)

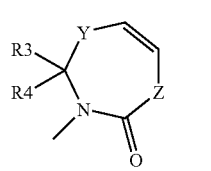

(6)

wherein M represents a saturated or unsaturated 5-to-7-membered ring having 0 to 4 hetero atoms selected from the group consisting of oxygen atoms, sulfur atoms and nitrogen atoms, substituents Ra, Rb, Rc and Rd may be the same or different from each other, and each represents a hydrogen atom, a halogen atom, a hydroxyl group, a lower alkyl group which may contain a hetero atom(s) in the chain thereof, a lower alkenyl group which may contain a hetero atom(s) in the chain thereof, a lower alkynyl group which may contain a hetero atom(s) in the chain thereof, a cycloalkyl group which may contain a hetero atom(s) in the ring thereof, an aryl group, a heteroaryl group, a lower alkyl group substituted with a cycloalkyl group(s) which may contain a hetero atom(s) in the ring thereof, a lower alkyl group substituted with an aryl group(s), a lower alkyl group substituted with a heteroaryl group(s), a lower alkoxyl group, a lower alkoxyl group substituted with a cycloalkyl group(s) which may contain a hetero atom(s) in the ring thereof, a lower alkoxyl group substituted with an aryl group(s), a lower alkoxyl group substituted with a heteroaryl group(s), a cycloalkyloxy group which may contain a hetero atom(s) in the ring thereof, an aryloxy group, a heteroaryloxy group, a lower hydroxyalkyl group, a lower hydroxyalkenyl group, a lower hydroxylalkoxyl group, a lower halogenoalkyl group, a lower halogenoalkoxyl group, a lower halogenoalkenyl group, nitro group, cyano group, a substituted or unsubstituted amino group, carboxyl group, a lower alkyloxycarbonyl group, a substituted or unsubstituted carbamoyl group, a lower alkanoyl group, an aroyl group, a lower alkylthio group, a lower alkylsulfonyl group, a substituted or unsubstituted sulfonylamino group or a substituted or unsubstituted sulfamoyl group, and Ra, Rb, Rc and Rd may form a ring between them, R3 and R4 are defined above in the general formula (2-1).

In the above-described general formula (1),

X represents $C(=O)$ or $C(-R3)(-R4)$, and particularly $C(=O)$ or methylene groups are preferred. Y represents an interatomic bond, $C(-R5)(-R6)$, $C(-R7)=C(-R8)$ or a lower alkyl chain, and the interatomic bond and $C(-R7)=C(-R8)$ are preferable, and particularly the interatomic bond is preferable. Z is preferably an interatomic bond.

Especially, in the general formula (2-1), the general formulae (5-1) and (5-2) are preferable in which R1 and R2 form a saturated or unsaturated ring with C=C on the ring represented by the general formula (2-1), and particularly the general formula (5-1) is preferable. The ring represented by M in the above general formulae (5-1) and (5-2) is preferably a saturated or unsaturated 5-to-7-membered ring having 0 to 4 hetero atoms selected from the group consisting of oxygen atoms, sulfur atoms and nitrogen atoms. Its examples are a phenyl group, a naphthyl group, a pyridyl group, a pyrazyl group and a cyclohexyl group.

Substituents Ra, Rb, Rc and Rd in the ring M may be the same or different from each other, and particularly a hydrogen atom, a halogen atom such as a fluoro group and a bromo group, a lower alkyl group and a nitro group are preferred.

In the present specification, when R1 and R2 are bonded together to form a saturated or unsaturated ring with C=C on the ring represented by the general formula (2-1), since the ring represented by M includes a double bond as shown in the general formula (2-1), the bond except the double bond in the ring represented by M is saturated or unsaturated.

In the general formula (6), R3 and R4 are preferably hydrogen atoms.

It is preferable that the group represented by B represents a hydroxyl group or a lower alkoxyl group, and more preferably a hydroxyl group.

The group represented by E is preferably a lower alkyl group or a hydrogen atom, more preferably a hydrogen atom.

The group represented by D is preferably an aryl group, a heteroaryl group and a cycloalkyl group which may contain a hetero atom(s) in the ring thereof. The aryl group, the heteroaryl group or the cycloalkyl group which may contain a hetero atom(s) in the ring thereof herein indicates a substituted or unsubstituted group. The substituents thereof are the same with those described in substituent Ra to Rd on the ring formed by the bond between the above-described R1 and R2.

In those described above, the group represented by D is particularly preferably a substituted or unsubstituted phenyl group, a substituted or unsubstituted pyridyl group or cyclohexyl group, and the substituents thereof are preferably 1 to 3 and more preferably 1 or 2 lower alkyl groups or lower alkoxyl group, a halogen atom, a nitro group, a substituted or unsubstituted amino group, a tetrazolyl group and a lower alkylsulfonylamino group.

The group represented by J and J' is preferably a hydrogen atom.

The group represented by T is preferably $C(=O)$.

In the general formula (1) in the present invention, it is preferable that A is the group represented by the general formula (5-1) or (5-2) wherein M represents a saturated or unsaturated 5-to-7-membered ring having 0 to 4 hetero atoms selected from the group consisting of oxygen atoms, sulfur atoms and nitrogen atoms.

In the general formula (1), it is preferable that Y is the group represented by an interatomic bond, A is the group represented by the general formula (5-1) or (5-2) wherein M represents a saturated or unsaturated 5-to-7-membered ring having 0 to 4 hetero atoms selected from the group consisting of oxygen atoms, sulfur atoms and nitrogen atoms.

In the general formula (1), it is preferable that Y is the group represented by $C(-R5)(-R6)$, A is the group represented by the general formula (5-1) or (5-2) wherein M represents a saturated or unsaturated 5-to-7-membered ring having 0 to 4 hetero atoms selected from the group consisting of oxygen atoms, sulfur atoms and nitrogen atoms.

In the general formula (1), it is preferable that A is the group represented by the general formula (6).

In the present invention, it is preferable that A is the following general formula (24):

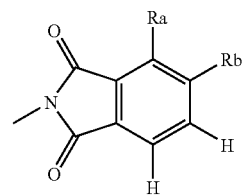

(24)

wherein Ra represents a hydrogen atom, a fluorine atom, a chloro atom, a bromo atom, a nitro group, an alkyl group having 1 to 3 carbon atoms or an alkoxyl group having 1 to 3 carbon atoms, Rb represents a hydrogen atom, a fluorine atom, a chloro atom, a bromo atom, a nitro group, an alkyl group having 1 to 3 carbon atoms, an amino group, an amino group substituted by one or two alkyl groups having 1 to 3 carbon atoms, a carbamoyl group or a carbamoyl group substituted by one or two alkyl groups having 1 to 3 carbon atoms, B represents a hydroxyl group or a lower alkoxyl group, E represents a hydrogen atom, D represents an aryl group which may have a substituent(s) or a heteroaryl group which may have a substituent(s), T represents $C(=O)$, J and J' represent a hydrogen atom.

In the present invention, it is also preferable that A is the following general formula (25-1), (25-2), (25-3) or (25-4):

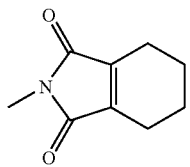
(25-1)

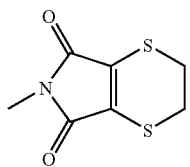
(25-2)

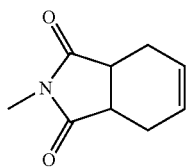
(25-3)

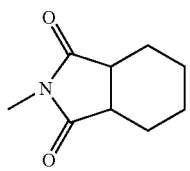
(25-4)

wherein B represents a hydroxyl group or a lower alkoxyl group,

E represents a hydrogen atom,

D represents an aryl group which may have a substituent(s) or a heteroaryl group which may have a substituent(s), T represents C(=O), J and J' represent a hydrogen atom.

In the present invention, it is further preferable that A is the following general formula (26-1), (26-2) or (26-3):

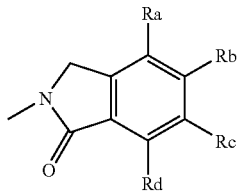
(26-1)

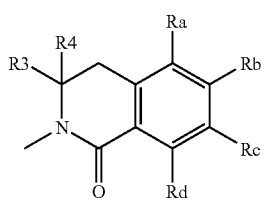
(26-2)

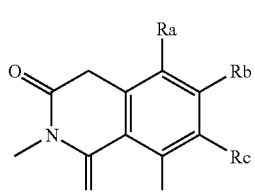
(26-3)

wherein Ra to Rd may be the same or different from each other, and each represents a hydrogen atom, a halogen atom, a hydroxyl group, a lower alkyl group which may contain a hetero atom(s) in the chain thereof, a lower alkenyl group which may contain a hetero atom(s) in the chain thereof, a lower alkynyl group which may contain a hetero atom(s) in the chain thereof, a cycloalkyl group which may contain a hetero atom(s) in the ring thereof, an aryl group, a heteroaryl group, a lower alkyl group substituted with a cycloalkyl group(s) which may contain a hetero atom(s) in the ring thereof, a lower alkyl group substituted with an aryl group(s), a lower alkyl group substituted with a heteroaryl group(s), a lower alkoxyl group, a lower alkoxyl group substituted with a cycloalkyl group(s) which may contain a hetero atom(s) in the ring thereof, a lower alkoxyl group substituted with an aryl group(s), a lower alkoxyl group substituted with a heteroaryl group(s), a cycloalkyloxy group which may contain a hetero atom(s) in the ring thereof, an aryloxy group, a heteroaryloxy group, a lower hydroxyalkyl group, a lower hydroxyalkenyl group, a lower hydroxyalkoxyl group, a lower halogenoalkyl group, a lower halogenoalkoxyl group, a lower halogenoalkenyl group, nitro group, cyano group, a substituted or unsubstituted amino group, carboxyl group, a lower alkyloxycarbonyl group, a substituted or unsubstituted carbamoyl group, a lower alkanoyl group, an aroyl group, a lower alkylthio group, a lower alkylsulfonyl group or a substituted or unsubstituted sulfamoyl group, and Ra, Rb, Rc and Rd may form a ring between them, B represents a hydroxyl group or a lower alkoxyl group, E represents a hydrogen atom, D represents an aryl group which may have a substituent(s) or a heteroaryl group which may have a substituent(s), T represents C(=O), J and J' represent a hydrogen atom.

In the present invention, it is furthermore preferable that A is the following general formula (27):

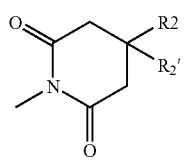
(27)

wherein R2 and R2' together form an alkylene group having 4 to 6 carbon atoms,

B represents a hydroxyl group or a lower alkoxyl group,

E represents a hydrogen atom,

D represents an aryl group which may have a substituent(s) or a heteroaryl group which may have a substituent(s), T represents C(=O), J and J' represent a hydrogen atom.

In any cases described above, D is more preferably 2,6-dichlorophenyl group, 2,6-dichloro-4-tetrazolyl-phenyl group, 2,6-dichloro-4-lower-alkylsulfonylamino-phenyl group or 3,5-dichloropyridine-4-yl group.

In the present invention, phenylalanine derivatives of the following structural formulae or pharmaceutically acceptable salts thereof are particularly preferable:

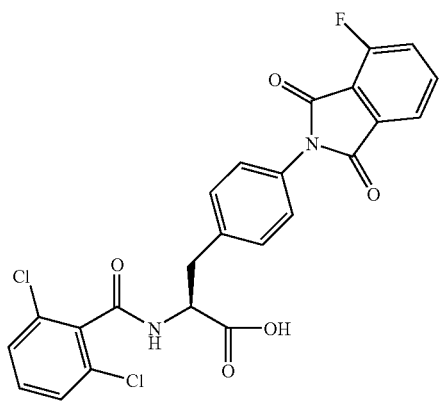
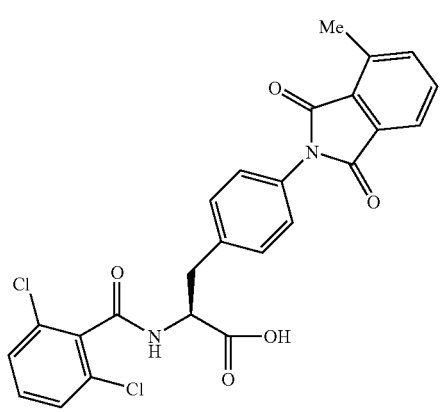
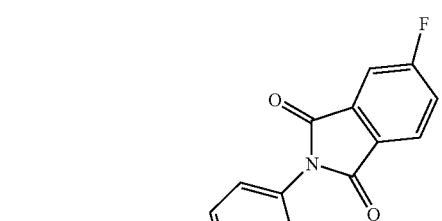
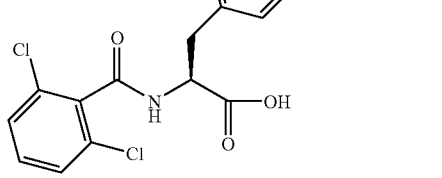
-continued
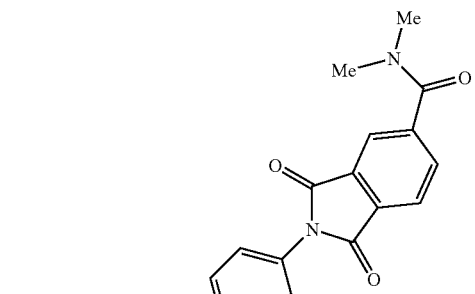
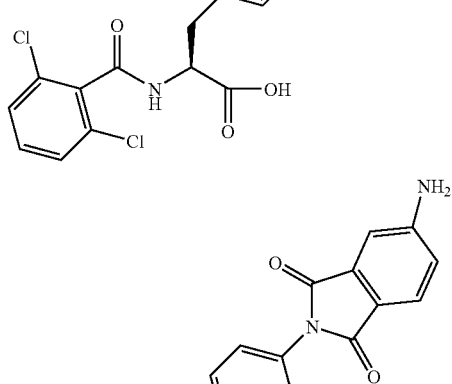
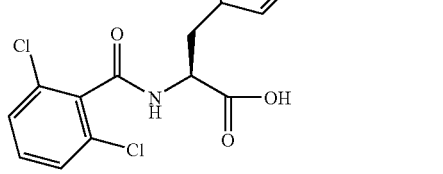
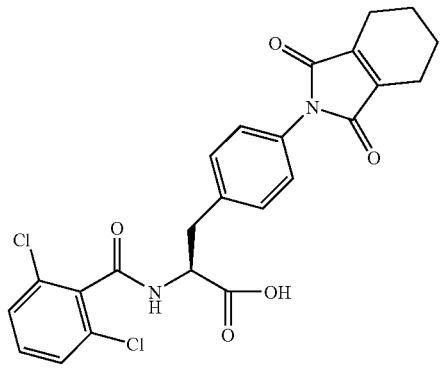
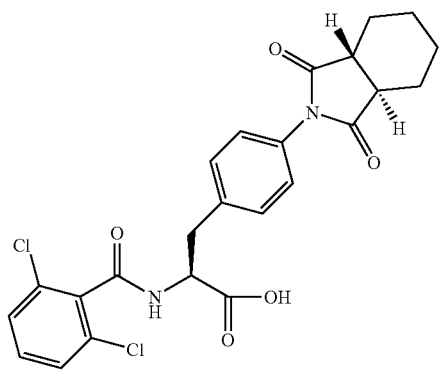

-continued

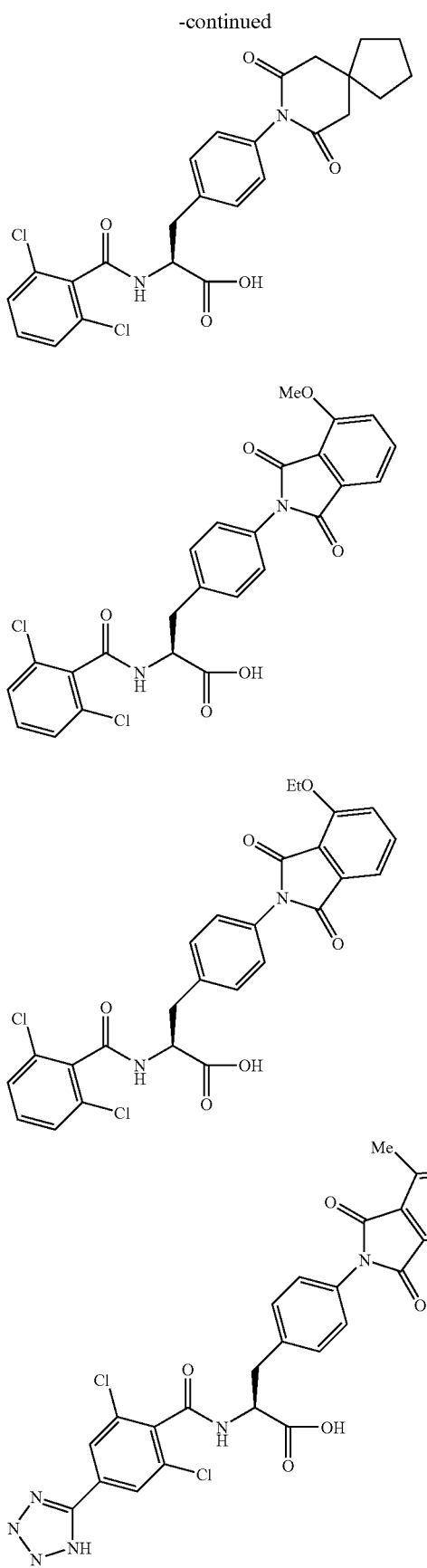

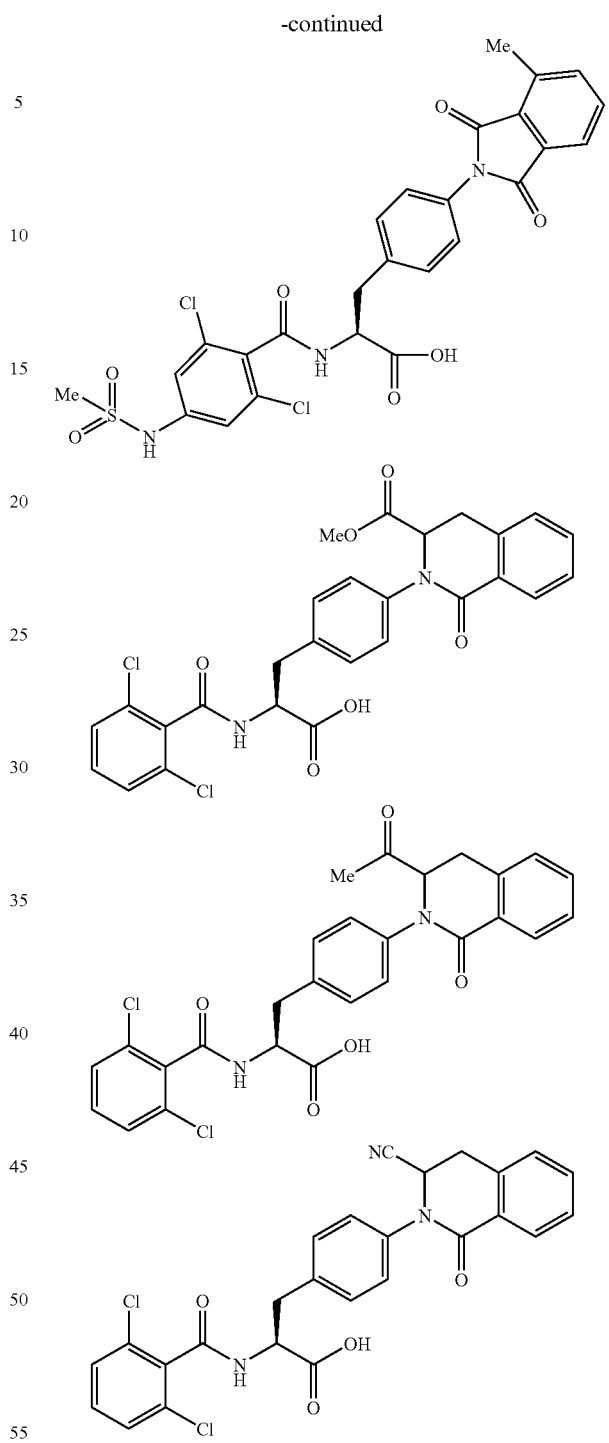

The phenylalanine derivatives (1) of the present invention can be synthesized, for example, by methods described below when B is a hydroxyl group.

Namely, a suitably protected carboxylic acid (7) is loaded into a resin by a usual method. The substituent P of the carboxylic acid (7) has a structure of E as described above with reference to the general formula (1), it is a substituent which can be converted into E in any of the synthesis or it is suitably protected form of these substituents. The substituent Q of the carboxylic acid (7) has a structure of D-T as described above with reference to the general formula (1), it is a substituent which can be converted into D-T in any stage of the synthesis or it is suitably protected form of these substituents. Further, the substituent R of the carboxylic acid (7) has a structure of a substituent which can be converted into NH₂ or suitably protected form of group of NH₂.

As for the loading reaction conditions, the reaction can be conducted by using, if necessary, a suitable additive such as HOAt (1-hydroxy-7-azabenzotriazole), HOBt (1-hydroxybenzotriazole) or DMAP (dimethylaminopyridine) and a condensing agent such as DIC (diisopropylcarbodiimide), DCC (dicyclohexylcarbodiimide) or EDC (1-ethyl-3-(3-dimethylaminopropyl)carbodiimide) in an organic solvent such as dichloromethane, DMF (N,N-dimethylformamide) or NMP (N-methyl-2-pyrrolidone). For example, when Wang resin is used, the reaction is carried out in the presence of pyridine and 2,6-dichlorobenzoyl chloride in DMF to obtain an ester (8). The ester (8) can be changed to an amine (9) under suitable conditions depending on the substituent R. For example, when a nitro group is used as R, the ester (8) can be changed to the amine (9) in the presence of a reducing agent such as SnCl₂ or hydrates thereof in a solvent such as NMP, DMF or ethanol. In the case of an amine protected with Fmoc group (9-fluorenylmethoxycarbonyl group) (FmocNH), the protective group can be removed with a base such as piperidine in a solvent such as DMF to obtain the amine (9).

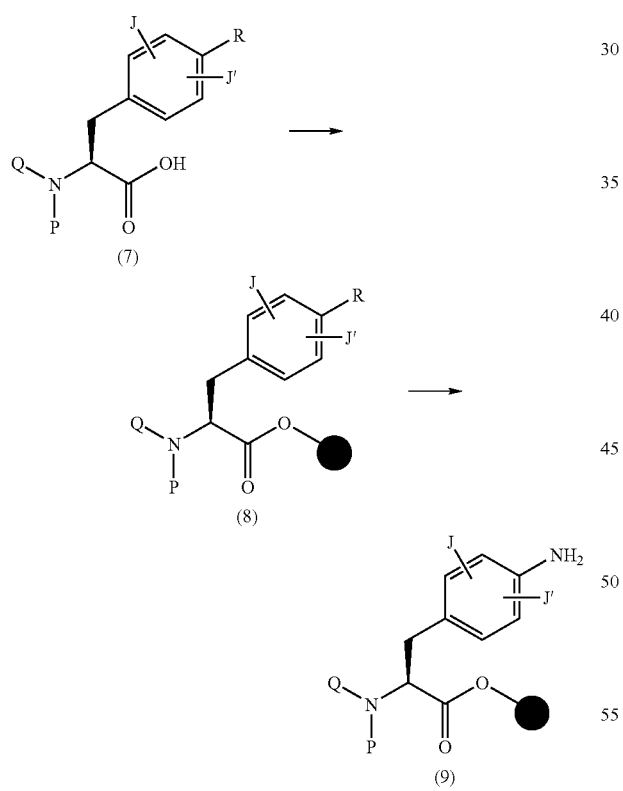

An imide (13) wherein A represents the general formula (2-1) and X represents C(=O) in the general formula (1) can be obtained by the following method. First, the amine (9) and a dicarboxylic anhydride (10) (under basic or neutral condition, reacted by warming) or the amine (9) and a dicarboxylic acid (11) are condensed with a reagent such as diisopropylcarbodiimide to obtain a monocarboxylic acid (12). Then, the said monocarboxylic acid (12) is warmed in a solvent such as toluene and acetic anhydride to introduce a ring closure reaction. Thus, the imide (13) can be synthesized. (2)a in the following structure represents a partial structure in the general formula (2-1):

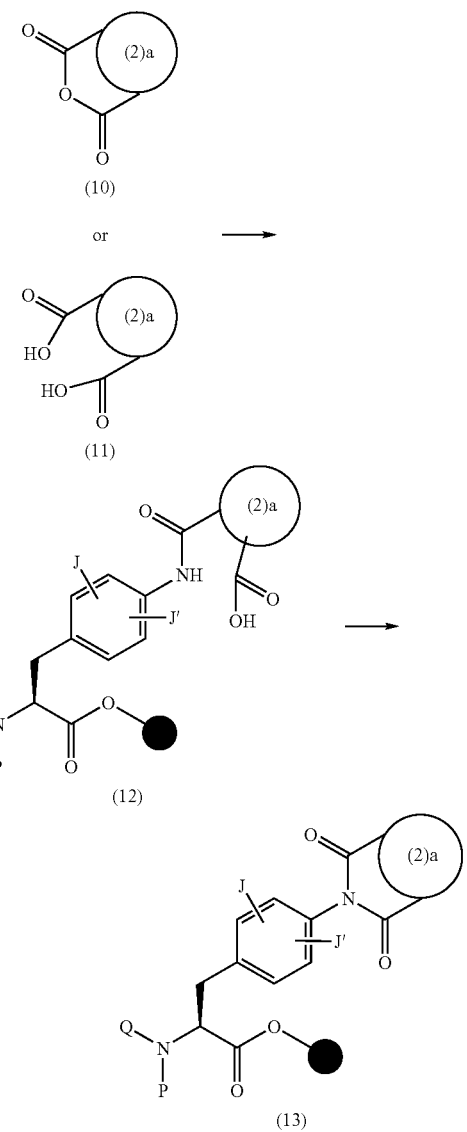

A lactam (15) wherein A represents the general formula (2-1) and X represents CH₂ in the general formula (1) can be obtained by heating and stirring the amine (9) and a dialdehyde (14) in a solvent such as toluene and benzene to introduce a ring closure reaction. (2)b in the following structure represents a partial structure in the general formula (2-1):

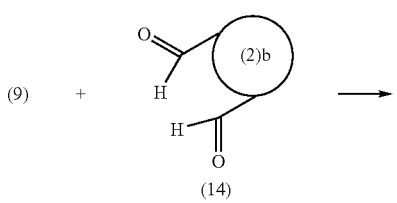

-continued

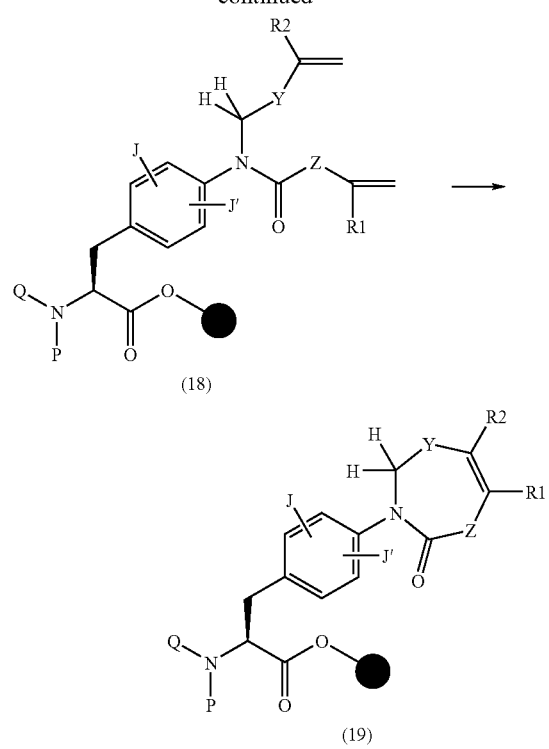

(18)

(19)

An lactam (19) wherein A represents the general formula (2-1), X represents CH$_2$ and R1 and R2 in the general formula (2-1) do not form a ring structure with C=C on the ring of the general formula (2) in the general formula (1) can be obtained by the following method. First, a nitrobenzenesulfonyl chloride, etc is reacted with the amine (9) under basic condition to obtain a nitrobenzenesulfonamide compound (Ns) (16). The said nitrobenzenesulfonamide compound (16) is reacted with alcohol having an olefin structure by Fukuyama-Mitsunobu reaction to obtain N-alkyl compound (17). The N-alkyl compound (17) can be also obtained by reacting a halide having an olefin structure with the nitrobenzenesulfonamide compound (16) under basic condition. The thus-obtained N-alkyl compound (17) is subjected to de-nitrobenzenesulfonyl reaction by a usual method. Then, the N-alkyl body (17) is acylated by a carboxylic acid or an acidic halide having an olefin structure to obtain a diolefin (18). The diolefin (18) is reacted with a ruthenium carbene complex in benzene or dichloromethane to obtain the objective lactam (19).

D-T part in the general formula (1) can be constructed as follows. For example, when T is C(=O) and B is a hydroxyl group in the general formula (1), if, in the ester (20), the substituent G has E structure, the substituent(s) which can be converted into E in a certain point of the synthesizing process or the substituent(s) which have suitably protected structure, then the substituent Z has the structure of (2-1) or (2-2) or the substituent(s) which can be converted into A in a certain point of the synthesizing process or the substituent(s) has suitably protected structure, the ester (20) can be converted in the amine (21) by removing a protective group(s) under suitable conditions depending on the protective group E. For instance, when Fmoc group (9-fluorenylmethoxycarbonyl group) is used as E, the protective groups can be removed with a base such as piperidine in a solvent such as DMF. The amine (21) can be converted into the amide (22) by condensing appropriate carboxylic acid by using a condensing agent such as DIC and, if necessary, a suitable additive such as HOAt or HOBt in an organic solvent such as DMF, NMP and dichloromethane.

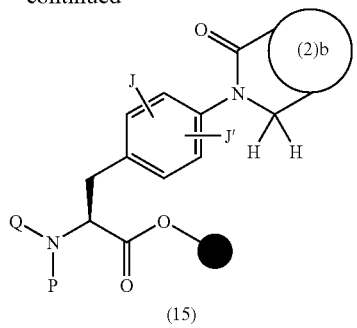

(9) → (16) →

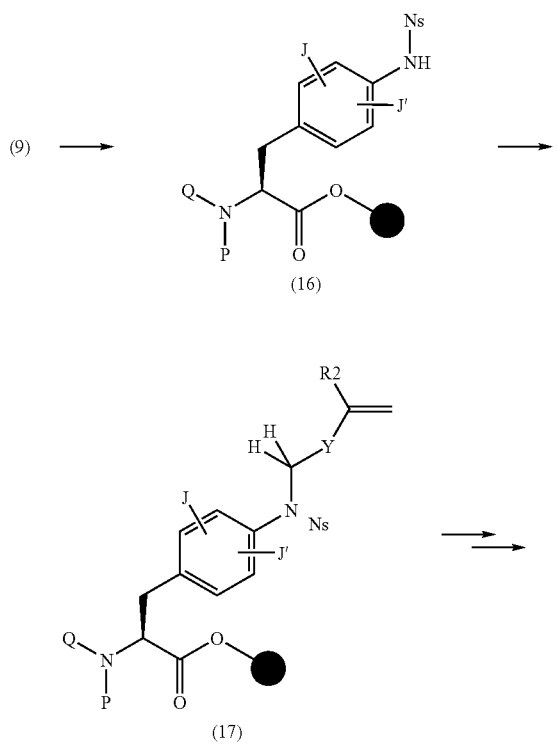

(17)

(20)

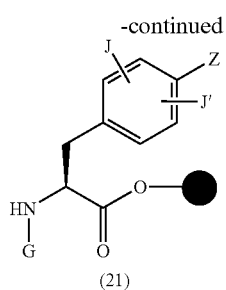

(21)

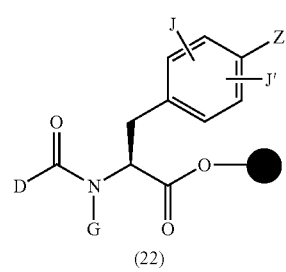

(22)

Further, the amine (21) is reacted with carboxylic acid halide, carboxylic anhydride, sulfonyl halide and sulfonyl anhydride under the existence of an organic base such as triethylamine, diisopropylethylamine, pyridine and N,N-dimethylaminopyridine or an inorganic base such as potassium carbonate and sodium carbonate in an organic solvent such as DMF, NMP and dichloromethane and then can form the corresponding amide structure and sulfonamide acid structure.

Further, the amine (21) is reacted with various isocyanate and isothiocyanate under the existence of an organic base, if necessary, such as triethylamine, diisopropylethylamine, pyridine and N,N-dimethylaminopyridine in an organic solvent such as DMF, toluene and dichloromethane and then can form the corresponding urea structure and thiourea structure.

The esters synthesized by the above-described methods such as (13), (15), (19), (22) and (23) are cleaved from a resin under suitable conditions to obtain a carboxylic acid (1). For example, when Wang resin is used, if, in the ester (23), each of A1, E1 and D1 is A, E, and D respectively or a group which is converted in A, E, and D respectively under the cleavage condition, the ester (23) is treated with an acidic solution including such as TFA (trifluoroacetic acid) thereto to obtain a solution of the carboxylic acid (1). The carboxylic acid (1) can be obtained by evaporating the solvent thereof. Further, the pure carboxylic acid (1) can be obtained by purification methods such as column chromatography, HPLC and recrystallization to the thus-obtained carboxylic acid (1).

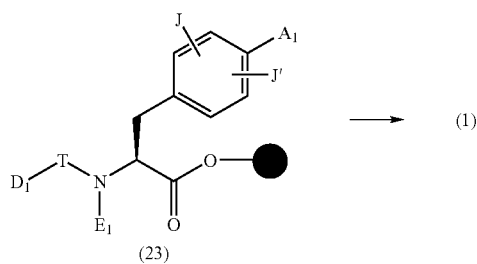

(23)

Because the phenylalanine derivatives of the general formula (1) of the present invention include asymmetric carbons, it can be considered that the phenylalanine derivatives of the general formula (1) of the present invention are optical isomers and the compound indicated in the present invention include the said optical isomers. Regarding the compound in which a diastereomer exists, the diastereomer and the diastereomer mixture are included in the said phenylalanine derivatives. Because the phenylalanine derivatives of the general formula (1) of the present invention include a mobile hydrogen atom, it can be considered that the phenylalanine derivatives of the general formula (1) of the present invention are a variety of tautomeric forms and the compound indicated in the present invention include the said tautomeric forms. Further, the carboxyl groups of the compound of the present invention may be substituted with appropriate substituents which are converted into a carboxyl group in vivo.

When the compounds of general formula (1) of the present invention can form salts thereof, it is sufficient for the salts to be pharmaceutically acceptable ones. When the compound in the formula has an acidic group such as carboxyl group, the salts can be ammonium salts, or salts thereof with alkali metals, e.g. sodium and potassium, salts thereof with alkaline earth metals, e.g. calcium and magnesium, salts thereof with aluminum and zinc, salts thereof with organic amines, e.g. triethylamine, ethanolamine, morpholine, piperidine and dicyclohexylamine, and salts thereof with basic amino acids, e.g. arginine and lysine. When the compound in the formula has a basic group, the salts can be those with inorganic acids, e.g. hydrochloric acid, sulfuric acid and phosphoric acid; those with organic carboxylic acids, e.g. acetic acid, citric acid, benzoic acid, maleic acid, fumaric acid, tartaric acid and succinic acid; and those with organosulfonic acids, e.g. methanesulfonic acid and p-toluenesulfonic acid. The salts can be formed by mixing a compound of the general formula (1) with a necessitated acid or base in a proper ratio in a solvent or dispersant or by the cation exchange or anion exchange reaction with another salt.

The compounds of the general formula (1) of the present invention include also solvates thereof such as hydrates and alcohol adducts thereof.

The compounds of general formula (1) and salts thereof are administered as they are or in the form of various pharmaceutical compositions to patients. The dosage forms of the pharmaceutical compositions are, for example, tablets, powders, pills, granules, capsules, suppositories, solutions, sugar-coated tablets, depots and syrups. They can be prepared with ordinary preparation assistants by an ordinary method.

For example, the tablets are prepared by mixing the phenylalanine derivative, the active ingredient of the present invention, with any of known adjuncts such as inert diluents, e.g. lactose, calcium carbonate and calcium phosphate; binders, e.g. acacia, corn starch and gelatin; extending agents, e.g. alginic acid, corn starch and pre-gelatinized starch; sweetening agents, e.g. sucrose, lactose and saccharin; flavour, e.g. peppermint and cherry; lubricants, e.g. magnesium stearate, talc and carboxymethyl cellulose; excipients for soft gelatin capsules and suppositories, e.g. fats, waxes, semi-solid or liquid polyols, natural oils and hardened oils; and excipients for solutions, e.g. water, alcohols, glycerols, polyols, sucrose, invert sugars, glucose and vegetable oils. It is preferable that the pharmaceutical compositions containing the phenylalanine derivatives of the present invention as the active ingredient include a pharmaceutically acceptable diluent and/or carrier.

The antagonist containing a compound(s) of above general formula (1) or a salt(s) thereof as active ingredient is usable as a therapeutic agent or preventing agent for diseases in which α 4 integrin-depending adhesion process participates in the pathology, such as inflammatory diseases, rheumatoid arthritis, inflammatory bowel diseases, systemic lupus erythematosus, multiple sclerosis, Sjögren's syndrome, asthma, psoriasis, allergy, diabetes, cardiovascular diseases, arterial sclerosis, restenosis, tumor proliferation, tumor metastasis, transplantation rejection, etc.

The dose of the compound of general formula (1) or salt thereof used for the above-described purpose varies depending on the intended therapeutic effect, administration method, period of the treatment, and age and body weight of the patient. The dose is usually 1 µg to 5 g a day for adults in the oral administration, and 0.01 µg to 1 g a day for adults in the parenteral administration.

The following Examples will further illustrate the present invention, which are only preferred embodiments of the invention and which by no means limit the invention.

EXAMPLE 1

Synthesis of the Compound of the Following General Formula (1-1)

Process 1 Preparation of Resin

Fmoc-Phe(4-nitro)-OH (2.5 g), 2,6-dichlorobenzoyl chloride (0.745 mL) and pyridine (1.5 mL) in a solution of NMP (25 mL) were added to Wang resin (0.76 mmol/g, 2.3 g) and stirred at room temperature for 16 hours. After removing the superfluous solvent, the resin was washed with DMF three times, dichloromethane three times and NMP twice. In order to do capping of a nonreactive hydroxyl group on the resin, the resin was treated with acetic anhydride (20 mL), pyridine (20 mL) and NMP (20 mL) for 2 hours. After removing the superfluous solvent, the resin was washed with DMF three times and dichloromethane three times, and dried under reduced pressure.

Process 2 Removal of Fmoc Group

A solution of 20% piperidine (25 mL) was added to the resin obtained in Process 1 and reacted for 10 minutes. After removing the solvent, a NMP solution of 20% piperidine (25 mL) was further added thereto and reacted for 10 minutes. After removing the solvent, the resin was washed with NMP and dichloromethane three times each, and dried under reduced pressure.

Process 3 Acylation Reaction 2,6-dichlorobenzoyl chloride (1.1 mL), 2,6-lutidine (1.6 mL) and NMP (26 mL) were added to 2.0 g of the resin obtained in Process 2 and reacted for 16 hours. After removing the superfluous solvent, the resin was washed with NMP and dichloromethane three times each, and dried under reduced pressure.

Process 4 Reduction of Nitro Group

NMP (30 mL).EtOH (1.5 mL) solution of stannic chloride dihydrate (15.0 g) was added to 1.5 g of the resin obtained in Process 3 and reacted at room temperature for 16 hours. After removing the reaction solvent, the resin was washed with NMP and dichloromethane three times each.

Process 5 Construction of Imide Ring 100 mg of the resin obtained in Process 4 was stirred in phthalic anhydride (500 mg) and a solution of benzene (32 ml) at 80° C. for 16 hours. After removing the reaction solvent, the resin was washed with dimethylsulfoxide, NMP and dichloromethane three times each, and dried under reduced pressure.

Process 6 Removal of Resin

The resin obtained in Process 5 was treated with trifluoroacetic acid containing 5% of water for 1 hour. After filtration, the resin was concentrated under reduced pressure. The resin was purified by high-pressure liquid chromatography (water/acetonitrile, each containing 0.05%/0.04% trifluoroacetic acid) to obtain 0.4 mg of the intended compound.

MS (ESI MH+): 4 8 3, 4 8 5
CHNO: C24H16Cl2N2O5

EXAMPLES 2 to 12

The compounds of Examples 2 to 12 in the following Table 1 were synthesized by the same procedure as that of Example 1 that corresponding acid anhydride reagents were used in Process 5 of Example 1.

EXAMPLE 13

The compound of Example 13 was synthesized by using a synthetic intermediate of Example 3. First, the resin (100 mg) was synthesized by the same procedure as Process 5 of Example 1 wherein 3-nitrophthalic anhydride was used. Then, NMP (10 mL).EtOH (0.5 mL) solution of stannic chloride dihydrate (1.0 g) was added to the resin and reacted at room temperature for 16 hours. After removing the reaction solvent, the resin was washed with NMP and dichloromethane three times each. NMP (5.0 mL) and allyl bromide (1.0 mL) were added to the obtained resin and reacted at 80° C. for 16 hours. After removing the reaction solvent, the resin was washed with dimethylsulfoxide, NMP and dichloromethane three times each, and dried under reduced pressure. The resin was treated with trifluoroacetic acid containing 5% of water for 1 hour. After filtration, the resin was concentrated under reduced pressure. The resin was purified by high-pressure liquid chromatography (water/acetonitrile, each containing 0.05%/0.04% trifluoroacetic acid) to obtain 0.7 mg of the intended compound.

MS (ESI MH+): 5 3 8, 5 4 0
CHNO: C27H21Cl2N3O5

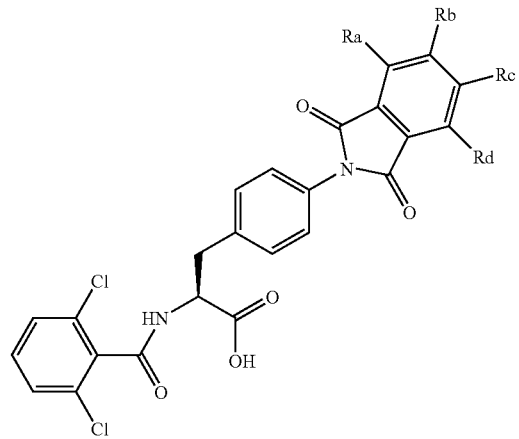

(1-1)

TABLE 1

| Example | Ra | Rb | Rc | Rd | MS Found (MH+) |
|---|---|---|---|---|---|
| 1 | H | H | H | H | 483, 485 |
| 2 | F | H | H | H | 501, 503 |
| 3 | NO2 | H | H | H | 528, 530 |
| 4 | Me | H | H | H | 497, 499 |
| 5 | OH | H | H | H | 499, 501 |
| 6 | H | Me | H | H | 497, 499 |
| 7 | H | Br | H | H | 562 |
| 8 | H | tert-Butyl | H | H | 539, 541 |
| 9 | H | NO2 | H | H | 528, 530 |
| 10 | H | Cl | Cl | H | 517, 519 |
| 11 | Cl | Cl | Cl | Cl | 619 |
| 12 | Br | Br | Br | Br | 799 |
| 13 | 2-Propenylamino | H | H | H | 538, 540 |
| 29 | H | F | H | H | 501, 503 |
| 30 | Me | H | H | Me | 511, 513 |
| 31 | Cl | H | H | Cl | 551, 553, 555 |
| 32 | H | COOH | H | H | 527, 529 |
| 33 | H | CON (Me) 2 | H | H | 554, 556 |
| 34 | H | CF3 | H | H | 551, 553 |
| 35 | H | NHAc | H | H | 540, 542 |
| 36 | H | NH2 | H | H | 498, 500 |
| 71 | NH2 | H | H | H | 498, 500 |
| 72 | Methoxy | H | H | H | 513, 515 |
| 73 | Ethoxy | H | H | H | 527, 529 |
| 74 | Benzyloxy | H | H | H | 589, 591 |
| 75 | Butoxy | H | H | H | 555, 557 |
| 76 | Isobutoxy | H | H | H | 554, 557 |
| 77 | H | OH | H | H | 499, 501 |
| 78 | H | Methoxy | H | H | 513, 515 |
| 79 | H | Ethoxy | H | H | 527, 529 |
| 80 | H | Benzyloxy | H | H | 589, 591 |
| 81 | H | Dimethylamino | H | H | 526, 528 |

EXAMPLE 14

Synthesis of the Compound of the Formula 1-2

Diphenic anhydride (1.0 g) and benzene (30 ml) were added to 300 mg of the resin obtained in Process 4 of Example 1 and stirred at 80° C. for 16 hours. After removing the reaction solvent, the resin was washed with dimethylsulfoxide, NMP and dichloromethane three times each. 20 mL of acetic anhydride was added to the obtained resin and stirred at 95° C. for 16 hours. After removing the reaction solvent, the resin was washed with dimethylsulfoxide, NMP and dichloromethane three times each, and dried under reduced pressure. The resin was treated with trifluoroacetic acid containing 5% of water for 1 hour. After filtration, the resin was concentrated under reduced pressure. The resin was purified by high-pressure liquid chromatography (water/acetonitrile, each containing 0.05%/0.04% trifluoroacetic acid) to obtain the intended compound.

MS (ESI MH+): 5 5 9, 5 6 1
CHNO: C30H20Cl2N2O5

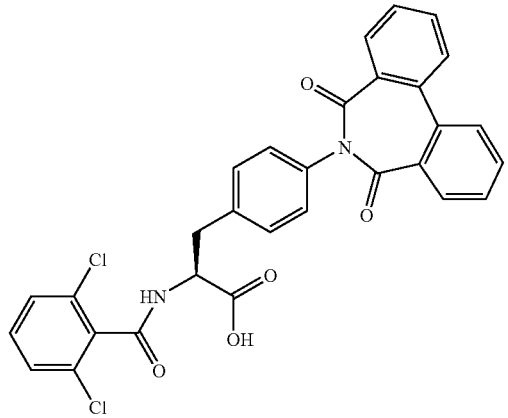

(1-2)

EXAMPLE 15

Synthesis of the Compound of the General Formula 1-3

Synthesis of the Formula (1-3-1)

The intended compound was synthesized by the same procedure as shown in Example 1 except that 100 mg of the resin obtained in Process 4 of Example 1 and homophthalic anhydride were used.

MS (ESI MH+): 4 9 7, 4 9 9
CHNO: C25H18Cl2N2O5

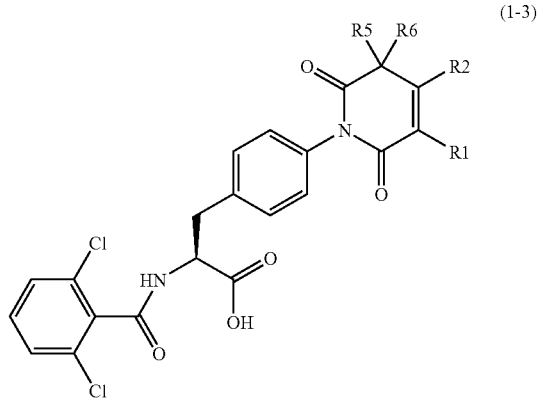

(1-3)

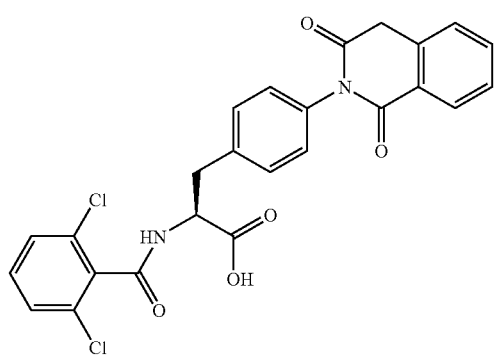

(1-3-1)

EXAMPLE 16

The intended compound having the following structural formula was synthesized by the same procedure as shown in Example 1 except that 100 mg of the resin obtained in Process 4 of Example 1 and 1,8-naphthalic anhydride were used.

MS (ESI MH+): 5 3 3, 5 3 5
CHNO: C28H18Cl2N2O5

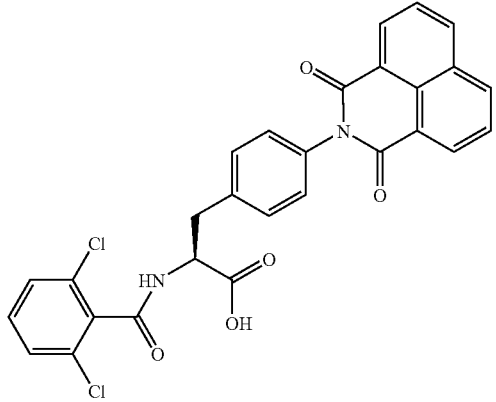
(1-3-2)

EXAMPLE 17

Synthesis of the Compound of the General Formula 1-4

Synthesis of the Formula (1-4-1)

300 mg of the resin obtained in Process 4 of Example 1 was stirred in ortho-phthalaldehyde (1.0 g) and a solution of benzene (30 ml) at 80° C. for 16 hours. After removing the reaction solvent, the resin was washed with dimethylsulfoxide, NMP and dichloromethane three times each, and dried under reduced pressure. The resin was treated with trifluoroacetic acid containing 5% of water for 1 hour. After filtration, the resin was concentrated under reduced pressure. The resin was purified by high-pressure liquid chromatography (water/acetonitrile, each containing 0.05%/0.04% trifluoroacetic acid) to obtain the intended compound.

MS (ESI MH+): 4 6 9, 4 7 1
CHNO: C24H18Cl2N2O4

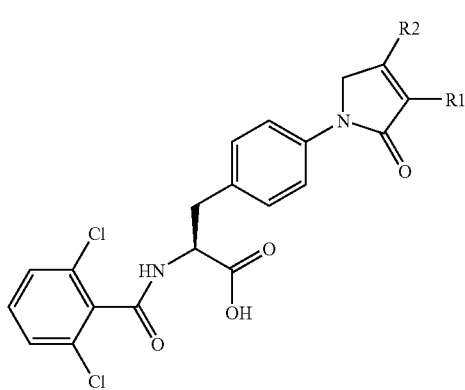
(1-4)

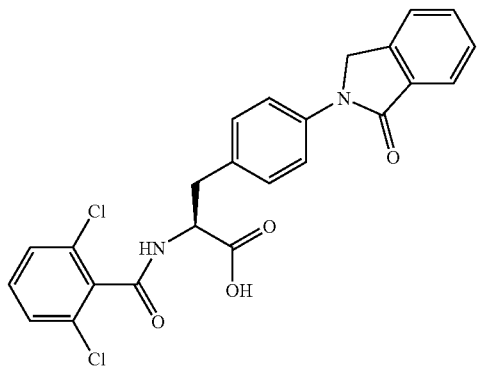
(1-4-1)

EXAMPLE 18

300 mg of the resin obtained in Process 4 of Example 1 was stirred in 2,3-thiophene-dicarboxyaldehyde (1.0 g) and a solution of benzene (30 ml) at 80° C. for 16 hours. After removing the reaction solvent, the resin was washed with dimethylsulfoxide, NMP and dichloromethane three times each, and dried under reduced pressure. The resin was treated with trifluoroacetic acid containing 5% of water for 1 hour. After filtration, the resin was concentrated under reduced pressure. The resin was purified by high-pressure liquid chromatography (water/acetonitrile, each containing 0.05%/0.04% trifluoroacetic acid) to obtain the intended mixture.

MS (ESI MH+): 4 7 5, 4 7 7
CHNOS: C22H16Cl2N2O4S

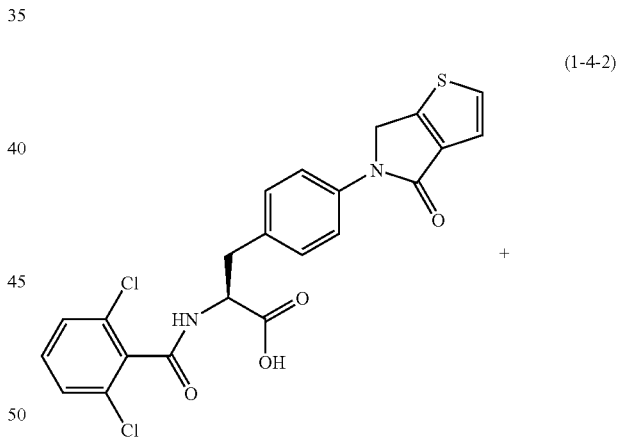
(1-4-2)

+

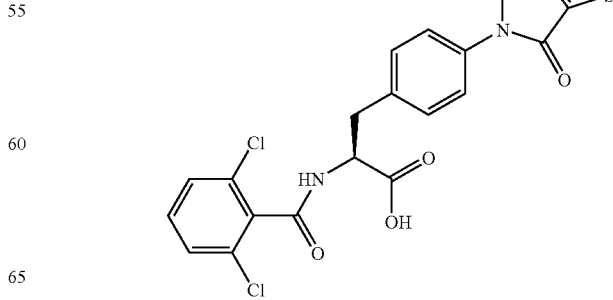

EXAMPLE 19

Synthesis of the Compound of the General Formula 1-5

The intended compound was synthesized by the same procedure as shown in Example 1 except that 100 mg of the resin obtained in Process 4 of Example 1 and 2,3-dimethylmaleic anhydride were used.

MS (ESI MH+): 4 6 1, 4 6 3
CHNO: C22H18Cl2N2O5

EXAMPLES 20 to 24

The compounds of Examples 20 to 24 were synthesized by the same procedure as shown in Example 1 except that 100 mg of the resin obtained in Process 4 of Example 1 and corresponding acid anhydride reagents were used in Process 5 of Example 1.

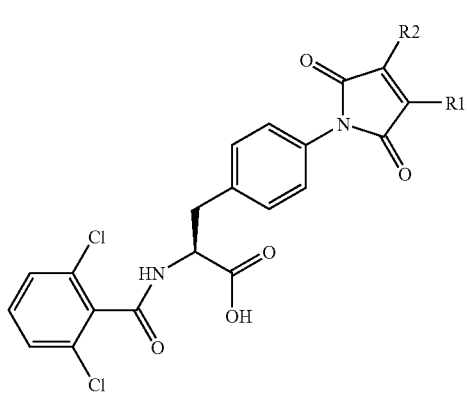
(1-5)

TABLE 2

| Example | R1 | R2 | MS Found (MH+) |
|---|---|---|---|
| 19 | Me | Me | 461, 463 |
| 20 | Ph | Ph | 585, 587 |

TABLE 2-continued

| Example | (structure) | MS Found (MH+) |
|---|---|---|
| 21 | phthalimide | 484, 486 |
| 22 | pyrazine-fused imide | 485, 487 |
| 23 | naphthalimide | 533, 535 |
| 24 | naphthalimide isomer | 533, 535 |

EXAMPLE 25

Synthesis of the Compound of the General Formula 1-6

200 mg of 2-nitrobenzenesulfonyl chloride and 400 μl of 2,6-lutidine were reacted in 2 ml of dichloromethane with 100 mg of the resin obtained in Process 4 of Example 1 and left at rest at 0° C. for 24 hours. After removing the reaction solvent, the resin was washed with dichloromethane, NMP and dichloromethane three times each. 200 ul of allyl bromide, 600 mg of potassium carbonate and 1 ml of NMP were added to the resin and the solution was shaken at 35° C. for 24 hours. After removing the reaction solvent, the resin was washed with dichloromethane, NMP and dichloromethane three times each, and dried under reduced pressure. 200 μl of DBU, 400 μl of 2-mercaptoethanol and 500 μl of NMP were added to the resin and shaken at room temperature for 24 hours. After removing the reaction solvent, the resin was washed with dichloromethane, NMP and dichloromethane three times each, and dried under reduced pressure. 20 ml of NMP, 100 mg of acrylic acid, 60 mg of HOAt and 70 ul of DIC were respectively added to the resin in this order and stirred at room temperature for 2.5 hours. After removing the reaction solvent, the resin was washed with NMP, dichloromethane, NMP and dichloromethane three times each and dried. 5 ml of dichloromethane was added to the resin. 20 mg of (benzylidene)-bis-(tricyclohexylphosphin) ruthenium (IV) dichloride was further added under argon atmosphere and stirred at room temperature for 24 hours. After removing the reaction solvent, the resin was washed with dichloromethane, NMP and dichloromethane three times each. The resin was treated with 100% trifluoroacetic acid for 1 hour. After filtering out the reaction liquid from the resin, the reaction liquid was concentrated and purified by reverse phase HPLC (SYMMETRY 19*50 mm mobile phase: water/acetonitrile, each containing 0.1% TFA) to obtain olefin metathesis product as the intended compound.

EXAMPLES 26 to 28

The compounds of Examples 26 to 28 were synthesized by the same procedure as shown in Example 25 except that 100 mg of the resin obtained in Process 4 of Example 1 and corresponding alkyl halide and carboxylic acid having an olefin structure were used.

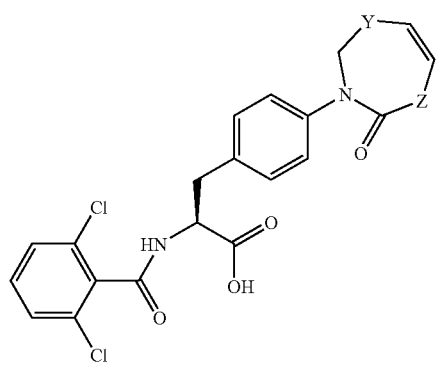

(1-6)

TABLE 3

| Example | Structure | MS Found (MH+) |
|---|---|---|
| 25 | | 419, 421 |
| 26 | | 433, 435 |
| 27 | | 447, 449 |

TABLE 3-continued

| Example | Structure | MS Found (MH+) |
|---|---|---|
| 28 | | 537, 539 |

EXAMPLES 29 to 32

The compounds of Examples 29 to 32 in the above-described Table 1 were synthesized by the same procedure as shown in Example 1 except that corresponding acid anhydride reagents were used in Process 5 of Example 1.

EXAMPLE 33

The compound of Example 33 was synthesized by using a synthetic intermediate of Example 32 of Table 1. First, the resin (100 mg) was synthesized by the same procedure as shown in Process 5 of Example 1 except that trimellitic [A.O.1] anhydride was used. Then, 20 ml of NMP, 100 µl of dimethylamine, 120 mg of HOAt and 140 µl of DIC were respectively added thereto in this order and stirred at room temperature for 2.5 hours. After removing the reaction solvent, the resin was washed with NMP, dichloromethane, NMP and dichloromethane three times each and dried. The resin was treated with trifluoroacetic acid containing 5% of water for 1 hour. After filtration, the resin was concentrated under reduced pressure. The resin was purified by high-pressure liquid chromatography (water/acetonitrile, each containing 0.05%/0.04% trifluoroacetic acid) to obtain 2.0 mg of the intended compound in Table 1.

EXAMPLE 34

20 ml of NMP, 100 mg of corresponding trifluoromethylphthalic acid, 120 mg of HOAt and 140 µl of DIC were respectively added to 50 mg of the resin obtained in Process 4 of Example 1 and stirred at room temperature for 12 hours. After removing the reaction solvent, the resin was washed with NMP, dichloromethane, NMP and dichloromethane three times each and dried. The resin was treated with trifluoroacetic acid containing 5% of water for 1 hour. After filtration, the resin was concentrated under reduced pressure. The resin was purified by high-pressure liquid chromatography (water/acetonitrile, each containing 0.05%/0.04% trifluoroacetic acid) to obtain 1.0 mg of the intended compound in Table 1.

EXAMPLE 35

The compound of Example 35 was synthesized by using a synthetic intermediate of Example 9 of Table 1. First, the resin (100 mg) was synthesized by the same procedure as shown in Process 5 of Example 1 except that 4-nitrophthalic anhydride was used. Then, NMP (10 mL). EtOH (0.5 mL) solution of stannic chloride dihydrate (1.0 g) was added to the resin and reacted at room temperature for 16 hours. After removing the reaction solvent, the resin was washed with NMP and dichloromethane three times each. NMP (5.0 mL), 1 ml of pyridine and 1 ml of acetic anhydride were added to the obtained resin and reacted at room temperature for 2 hours. After removing the reaction solvent, the resin was washed with dimethylsulfoxide, NMP and dichloromethane three times each, and dried under reduced pressure. The resin was treated with trifluoroacetic acid containing 5% of water for 1 hour. After filtration, the resin was concentrated under reduced pressure. The resin was purified by high-pressure liquid chromatography (water/acetonitrile, each containing 0.05%/0.04% trifluoroacetic acid) to obtain 3.2 mg of the intended compound in Table 1.

EXAMPLE 36

The compound of Example 36 was synthesized by using a synthetic intermediate of Example 35 of Table 1. The resin obtained by reacting stannic chloride dihydrate in Example 35 was treated with trifluoroacetic acid containing 5% of water for 1 hour. After filtration, the resin was concentrated under reduced pressure. The resin was purified by high-pressure liquid chromatography (water/acetonitrile, each containing 0.05%/0.04% trifluoroacetic acid) to obtain 0.2 mg of the intended compound in Table 1.

EXAMPLE 37

Synthesis of the Compound of the General Formula 1-7

Process 1 Preparation of Resin

Fmoc-Phe(4-nitro)-OH (2.5 g), 2,6-dichlorobenzoyl chloride (0.745 mL) and pyridine (1.5 mL) in a solution of NMP (25 mL) were added to Wang resin (0.76 mmol/g, 2.3 g) and stirred at room temperature for 16 hours. After removing the superfluous solvent, the resin was washed with DMF three times, dichloromethane three times and NMP twice. In order to do capping of a nonreactive hydroxyl group on the resin, the resin was treated with acetic anhydride (20 mL), pyridine (20 mL) and NMP (20 mL) for 2 hours. After removing the superfluous solvent, the resin was washed with DMF three times and dichloromethane three times, and dried under reduced pressure.

Process 2 Removal of Fmoc Group

A solution of 20% piperidine (25 mL) was added to the resin obtained in Process 1 and reacted for 10 minutes. After removing the solvent, a NMP solution of 20% piperidine (25 mL) was further added and reacted for 10 minutes. After removing the solvent, the resin was washed with NMP and dichloromethane three times each, and dried under reduced pressure.

Process 3 Acylation Reaction 2,6-dichlorobenzoyl chloride (1.1 mL), 2,6-lutidine (1.6 mL) and NMP (26 mL) were added to 2.0 g of the resin obtained in Process 2 and reacted for 16 hours. After removing the superfluous solvent, the resin was washed with NMP and dichloromethane three times each, and dried under reduced pressure.

Process 4 Reduction of Nitro Group

NMP (30 mL).EtOH (1.5 mL) solution of stannic chloride dihydrate (15.0 g) was added to 1.5 g of the resin obtained in Process 3 and reacted at room temperature for 16 hours. After removing the reaction solvent, the resin was washed with NMP and dichloromethane three times each.

Process 5 Construction of Imide Ring 100 mg of the resin obtained in Process 4 was stirred in a solution of 3,4,5,6-tetrahydrophthalic anhydride (500 mg) and benzene (32 ml) at 80° C. for 16 hours. After removing the reaction solvent, the resin was washed with dimethylsulfoxide, NMP and dichloromethane three times each, and dried under reduced pressure. 20 mL of acetic anhydride was added to the resin and stirred at 95° C. for 16 hours. After removing the reaction solvent, the resin was washed with dimethylsulfoxide, NMP and dichloromethane three times each, and dried under reduced pressure.

Process 6 Removal of Resin

The resin obtained in Process 5 was treated with trifluoroacetic acid containing 5% of water for 1 hour. After filtration, the resin was concentrated under reduced pressure. The resin was purified by high-pressure liquid chromatography (water/acetonitrile, each containing 0.05%/0.04% trifluoroacetic acid) to obtain 7.8 mg of the intended compound.

MS (ESI MH+): 4 8 7, 4 8 9

CHNO: C24H20Cl2N2O5

EXAMPLES 38 to 51

The compounds of Examples 38 to 51 were synthesized by the same procedure as shown in Example 37 except that corresponding acid anhydride reagents were used in Process 5 of Example 37.

EXAMPLES 52 to 54

The compounds of Examples 52 to 54 were synthesized by the same procedure as shown in Example 14 except that corresponding acid anhydride reagents were used.

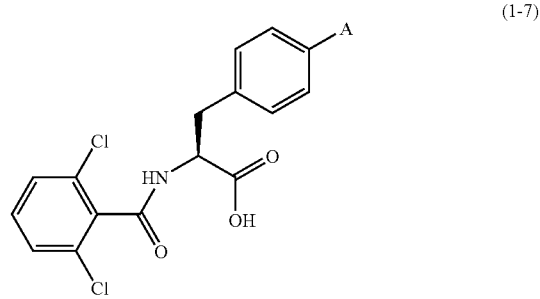

TABLE 4

| Example | A | MS Found (MH+) |
|---|---|---|
| 37 |  | 487, 489 |

TABLE 4-continued

| Example | A | MS Found (MH+) |
|---|---|---|
| 38 | | 523, 525 |
| 39 | | 473, 475 |
| 40 | | 489, 491 |
| 41 | | 489, 491 |
| 42 | | 499, 501 |
| 43 | | 503, 505 |
| 44 | | 513, 515 |
| 45 | | 487, 489 |

TABLE 4-continued

| Example | A | MS Found (MH+) |
|---|---|---|
| 46 | | 447, 449 |
| 47 | | 565, 567 |
| 48 | | 503, 505 |
| 49 | | 517, 519 |
| 50 | | 501, 503 |
| 51 | | 511, 513 |
| 52 | | 577, 479 |

TABLE 4-continued

| Example | A | MS Found (MH+) |
|---|---|---|
| 53 | | 525, 527 |
| 54 | | 477, 479 |
| 82 | | 511, 513 |

EXAMPLE 55

Synthesis of the Compound of the Formula 1-8

Process 1 Synthesis of Boc-Phe(4-NO$_2$)—OEt 5 g of Boc-Phe(4-NO$_2$)—OH, 3.09 g of 1-(3-dimethylaminopropyl)-3-ethylcarbodiimide hydrochloride, 5 ml of ethanol and 2 g of dimethylaminopyridine were stirred in dichloromethane for 3 days. The obtained substance was washed with 1N hydrochloric acid, an aqueous solution of saturated sodium hydrogen carbonate and saturated NaCl solution, and dried with magnesium sulfate. The solvent was removed to obtain the title compound.

Yield: 4.6 g

H-NMR (CDCl$_3$) δ 1.25 (3H, t), 1.40 (9H, s), 3.05-3.35 (2H, m), 4.20 (2H, q), 4.60 (1H, m), 5.10 (1H, br), 7.35 (2H, d), 8.15 (2H, d).

Process 2 Boc-Phe(4-NH$_2$)—OEt

A mixture of 4.6 g of Boc-Phe(4-NO$_2$)—Oet, 900 mg of 10% palladium carbon (containing 50% water) and ethanol was stirred overnight under hydrogenous atmosphere. After Celite filtration, the solvent was removed to obtain the title compound.

Yield: 4.4 g

H-NMR (CDCl$_3$) δ 1.25 (3H, t), 1.40 (9H, s), 2.95 (2H, br), 4.15 (2H, q), 4.45 (1H, m), 4.95 (1H, br), 6.60 (2H, d), 6.95 (2H, d).

Process 3 Synthesis of (2S)-2-amino-3-[4-(4-methyl-1,3-dioxo-1,3-dihydroisoindole-2-yl)phenyl]propionic acid ethylester hydrochloride The mixture of 2.75 g of Boc-Phe(4-NH$_2$)—OEt, 1.67 g of 3-methylphthalic anhydride and 40 mg of benzene was heat-refluxed. After adding ethyl acetate, the mixture was washed with 1N hydrochloric acid, an aqueous solution of 1N sodium hydroxide and saturated NaCl solution respectively, and dried with magnesium sulfate. The solvent was removed and the residue was washed with hexane to obtain (2S)-2-(t-butoxyamino)-3-[4-(4-methyl-1,3-dioxo-1,3-dihydroisoindole-2-yl)phenyl]propionic acid ethylester. Dioxane containing 4N hydrogen chloride was added thereto and stirred for 2 hours. The solvent was removed and the residue was washed with ethyl acetate to obtain the title compound.

Yield: 1.9 g

H-NMR (DMSO-d6) δ 1.15 (3H, m), 2.65 (3H, s), 3.10-3.40 (2H, m), 4.15 (2H, m), 4.30 (1H, t), 7.40 (4H, s), 7.65-7.80 (3H, m), 8.70 (3H, br).

Process 4 Synthesis of (2S)-2-(2-chloro-6-methyl-benzoylamino)-3-[4-(4-methyl-1,3-dioxo-1,3-dihydroisoindole-2-yl)phenyl]propionic acid ethylester The mixture of 88.2 mg of 2-chloro-6-methyl benzoic acid, 99.1 mg of 1-(3-dimethylaminopropyl)-3-ethylcarbodiimide hydrochloride, 79.1 mg of 1-hydroxybenzotriazol hydrate, 107 μl of triethylamine, 100 mg of (2S)-2-amino-3-[4-(4-methyl-1,3-dioxo-1,3-dihydroisoindole-2-yl)phenyl]propionic acid ethylester hydrochloride and 1 ml of dichloromethane was stirred at 45° C. overnight. The mixture was purified by silica gel chromatography to obtain the title compound.

Yield: 110.6 mg

MS (ESI, m/z) 503 (M-H)—

Process 5 Synthesis of (2S)-2-(2-chloro-6-methyl-benzoylamino)-3-[4-(4-methyl-1,3-dioxo-1,3-dihydroisoindole-2-yl)phenyl]propionic acid The mixture of (2S)-2-(2-chloro-6-methyl-benzoylamino)-3-[4-(4-methyl-1,3-dioxo-1,3-dihydroisoindole-2-yl)phenyl]propionic acid ethylester and 3N hydrochloric acid was stirred at 80° C. overnight. The solvent was removed and the residue was purified by reverse phase HPLC to obtain the title compound.

MS (ESI, m/z) 477 (MH+)

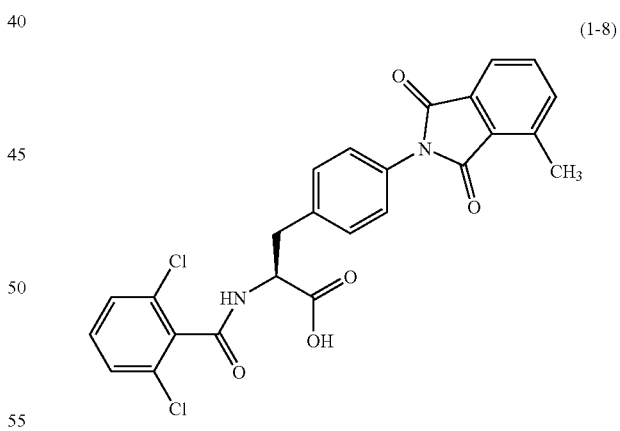

(1-8)

EXAMPLES 56 to 63

Synthesis of the Compound of the General Formula 1-9

The compounds of Examples 56 to 63 were synthesized by the same procedure as shown in Process 4 and 5 of Example 55 except that corresponding carboxylic reagents were used.

Meanwhile, substituted benzoic acid in the following Table 5 was synthesized as follows.

REFERENCIAL EXAMPLE 1

Synthesis of 2-chloro-6-trifuluoromethylbenzoic acid

The mixture of 500 mg of 3-chlorobenzotrifuluoride and 3 ml of tetrahydrofuran was cooled down to −50° C. and 2 ml of 1.6M n-butyllithium hexan solution was added and stirred for 1 hour. The mixture was put into dry ice and diluted by an aqueous solution of 1N sodium hydroxide. After washing it with toluene, the water layer was made acidic by hydrochloric acid and extracted with ethyl acetate. The residue obtained by removing the solvent was purified by reverse phase HPLC to obtain the title compound.

Yield: 244 mg

H-NMR (DMSO-d6) δ 7.68 (1H, t), 7.80 (1H, d), 7.88 (1H, d).

MS (ESI, m/z) 223 (M-H)—

REFERENCIAL EXAMPLE 2

Synthesis of 2-bromo-6-chlorobenzoic acid

The mixture of 500 mg of 3-bromochlorobenzen and 3 ml of tetrahydrofuran was cooled down to −78° C. and 1.3 ml of 2.0M lithiumdiisopropylamide heptane/tetrahydrofuran/ethylbenzene solution was added. After stirring it for 2 hours, the mixture was put into dry ice and washed and extracted as described in Referencial Example 1 to obtain a crude material. The crude material was washed with a mixed solvent of hexane-ethyl acetate to obtain the title compound.

Yield: 317 mg

H-NMR (DMSO-d6) δ 7.40 (1H, t), 7.60 (1H, d), 7.70 (1H, d).

MS (ESI, m/z) 233 (M-H)—

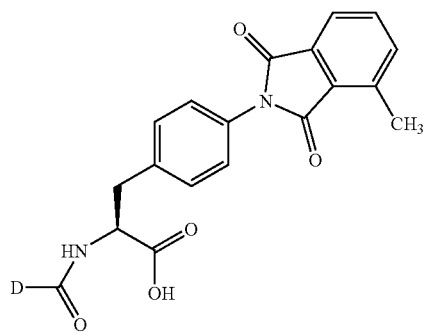

(1-9)

TABLE 5

| Example | D | MS Found (MH+) |
|---|---|---|
| 56 | 2-Cl, 6-CF3 phenyl | 531 |
| 57 | 2-Cl, 6-Br phenyl | 541 |
| 58 | 2-Cl, 6-F phenyl | 481 |
| 59 | 3,5-dichloropyridin-4-yl | 498 |
| 60 | 2-Cl, 3-Cl, 6-CH3 phenyl | 511 |
| 61 | 2,3,6-trichlorophenyl | 531 |
| 62 | 2,3,5-trichlorophenyl | 531 |
| 63 | 2-Cl, 3-Br, 6-NO2 phenyl | 542 |
| 83 | 3,5-dichloro-4-(1H-tetrazol-5-yl)phenyl | 563 (M − H)− |

TABLE 5-continued

| Example | D | MS Found (MH+) |
|---|---|---|
| 84 | H₃C-S(O)(O)-NH-(2,6-diCl-phenyl)-* | 588 (M − H)− |

EXAMPLE 64

The compound (10 mg) obtained in Example 4 was suspended in 0.5 ml of methanol. 2.0M trimethylsilyldiazomethane hexane solution (0.303 ml) was added and left at room temperature for 30 minutes. The reaction mixture was concentrated under reduced pressure to obtain 10 mg of the intended compound in Table 6.
MS (ESI MH+): 5 1 1, 5 1 3
CHNO: C26H20Cl2N2O5

EXAMPLE 65

The compound (10 mg) obtained in Example 6 was suspended in 0.5 ml of methanol. 2.0M trimethylsilyldiazomethane hexane solution (0.303 ml) was added and left at room temperature for 30 minutes. The reaction mixture was concentrated under reduced pressure and purified by high-pressure liquid chromatography (water/acetonitrile, each containing 0.05%/0.04% trifluoroacetic acid) to obtain 3 mg of the intended substance in Table 6.
MS (ESI MH+): 5 1 1, 5 1 3
CHNO: C26H20Cl2N2O5

EXAMPLE 66

The compound (10 mg) obtained in Example 1 was suspended in 0.5 ml of methanol. 2.0M trimethylsilyldiazomethane hexane solution (0.303 ml) was added and left at room temperature for 30 minutes. The reaction mixture was concentrated under reduced pressure and purified by high-pressure liquid chromatography (water/acetonitrile, each containing 0.05%/0.04% trifluoroacetic acid) to obtain 3 mg of the intended substance in Table 6.
MS (ESI MH+): 4 9 7, 4 9 9
CHNO: C25H18Cl2N2O5

EXAMPLE 67

The compound (10 mg) obtained in Example 29 was suspended in 0.5 ml of methanol. 2.0M trimethylsilyldiazomethane hexane solution (0.303 ml) was added and left at room temperature for 30 minutes. The reaction mixture was concentrated under reduced pressure and purified by high-pressure liquid chromatography (water/acetonitrile, each containing 0.05%/0.04% trifluoroacetic acid) to obtain 3.5 mg of the intended substance in Table 6.
MS (ESI MH+): 5 1 5, 5 1 7
CHNO: C25H17Cl2FN2O5

EXAMPLE 68

The compound (10 mg) obtained in Example 38 was suspended in 0.5 ml of methanol. 2.0M trimethylsilyldiazomethane hexane solution (0.303 ml) was added and left at room temperature for 30 minutes. The reaction mixture was concentrated under reduced pressure and purified by high-pressure liquid chromatography (water/acetonitrile, each containing 0.05%/0.04% trifluoroacetic acid) to obtain 4 mg of the intended substance in Table 6.
MS (ESI MH+): 5 3 7, 5 3 9
CHNO: C23H18Cl2N2O5S2

EXAMPLE 69

The compound (9.5 mg) obtained in Example 48 was suspended in 0.475 ml of methanol. 2.0M trimethylsilyldiazomethane hexane solution (0.288 ml) was added and left at room temperature for 30 minutes. The reaction mixture was concentrated under reduced pressure and purified by high-pressure liquid chromatography (water/acetonitrile, each containing 0.05%/0.04% trifluoroacetic acid) to obtain 3 mg of the intended substance in Table 6.
MS (ESI MH+): 5 1 7, 5 1 9
CHNO: C26H26Cl2N2O5

EXAMPLE 70

The compound (4.4 mg) obtained in Example 37 was suspended in 0.22 ml of methanol. 2.0M trimethylsilyldiazomethane hexane solution (0.133 ml) was added and left at room temperature for 30 minutes. The reaction mixture was concentrated under reduced pressure and purified by high-pressure liquid chromatography (water/acetonitrile, each containing 0.05%/0.04% trifluoroacetic acid) to obtain 2 mg of the intended substance in Table 6.
MS (ESI MH+): 5 0 1, 5 0 3
CHNO: C25H22Cl2N2O5

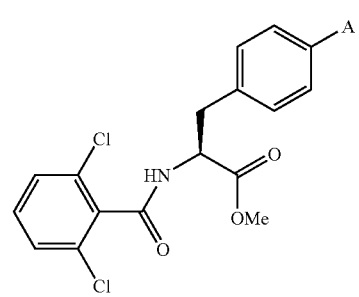

(1-10)

TABLE 6

| Example | A | MS Found (MH+) |
|---|---|---|
| 64 | N-methyl-4-methyl-phthalimide-* | 511, 513 |
| 65 | N-*-5-methyl-phthalimide | 511, 513 |

TABLE 6-continued

| Example | A | MS Found (MH+) |
|---|---|---|
| 66 | phthalimide structure | 497, 499 |
| 67 | fluoro-phthalimide structure | 515, 517 |
| 68 | dithiino-fused pyrrolidinedione structure | 537, 539 |
| 69 | spirocyclopentane piperidinedione structure | 517, 519 |
| 70 | tetrahydroisoindole-1,3-dione structure | 501, 503 |

The compounds of Examples 71 to 81 in Table 1 were synthesized by the following methods.

EXAMPLE 71

The compound of Example 71 was synthesized by using a synthetic intermediate of Example 3. 2.3 mg of the intended substance was obtained by the same procedure as shown in Example 36 except that a corresponding reagent was used.

EXAMPLE 72

2 ml of toluene, 250 ul of tri-n-butylphosphine and 46 ul of methanol were added to 100 mg of the resin having a phenol partial structure that is a synthetic intermediate of Example 5 and stirred at 0° C. for 1 hour. 505 ul of azodicarboxylic acid diisopropylester solution (containing 40% of the said substance in toluene) was further added and stirred at room temperature for 1 hour. After removing the reaction solvent, the resin was washed with dimethylsulfoxide, NMP and dichloromethane three times each, and dried under reduced pressure. The resin was treated with trifluoroacetic acid containing 5% of water for 1 hour. After filtration, the resin was concentrated under reduced pressure. The resin was purified by high-pressure liquid chromatography (water/acetonitrile, each containing 0.05%/0.04% trifluoroacetic acid) to obtain 10.0 mg of the intended substance.

EXAMPLES 73 TO 76

The compounds of Examples 73 to 76 were synthesized by using a synthetic intermediate of Example 3. The intended substances were obtained by the same procedure as that of Example 72 that corresponding reagents were used.

EXAMPLE 77

13.5 mg of the intended substance was obtained by the same procedure as shown in Example 5 except that a corresponding reagent was used.

EXAMPLES 78 TO 80

The compounds of Examples 78 to 80 were synthesized by using a synthetic intermediate of Example 77. The intended substances were obtained by the same procedure as shown in Example 72 except that corresponding reagents were used.

EXAMPLE 81

The intended substance was obtained by the same procedure as shown in Example 1 except that a corresponding reagent was used.

EXAMPLE 82

The compound of Example 82 in the above-described Table 6 was synthesized by the same procedure as shown in Example 37 except that a corresponding reagent was used to obtain 1.0 mg of the intended substance.

EXAMPLE 83

Synthesis of (2S)-2-(2,6-dichloro-4-tetrazolyl-benzoyl amino)-3-[4-(4-methyl-1,3-dioxo-1,3-dihydroisoindole-2-yl)phenyl]propionic acid Process 1 (2S)-2-(2,6-dichloro-4-tetrazolyl-benzoylamino)-3-[4-(4-methyl-1,3-dioxo-1,3-dihydroisoindole-2-yl)phenyl]propionic acid ethylester The mixture of 35 mg of 2,6-dichloro-4-tetrazolyl benzoic acid, 30 mg of 1-(3-dimethylaminopropyl)-3-ethylcarbodiimide hydrochloride, 23 mg of 1-hydroxybenzotriazol hydrate, 15 mg of triethylamine, 35 mg of (2S)-2-amino-3-[4-(4-methyl-1,3-dioxo-1,3-dihydroisoindole-2-yl)phenyl] propionic acid ethylester hydrochloride and 5 ml of dichloromethane was stirred at room temperature for 3 days. The mixture was concentrated and suspended in a mixed solvent of water-acetonitrile containing 0.1% trifluoroacetic acid and then filtered to obtain the title compound.

Yield: 22 mg

MS (ESI, m/z) 591 (M-H)—

Process 2 (2S)-2-(2,6-dichloro-4-tetrazolyl-benzoylamino)-3-[4-(4-methyl-1,3-dioxo-1,3-dihydroisoindole-2-yl)phenyl]propionic acid The mixture of 22 mg of (2S)-2-(2,6-dichloro-4-tetrazolyl-benzoylamino)-3-[4-(4-methyl-1,3-dioxo-1,3-dihydroisoindole-2-yl)phenyl]propionic acid ethylester, 10 ml of dioxane solution containing 4N hydrogen chloride and 10 ml of water was stirred at 80° C. overnight. After removing the solvent, the residue was purified by reverse phase HPLC to obtain the title compound (that of Example 83 in Table 7).
Yield: 19 mg
MS (ESI, m/z) 563 (M-H)—
Meanwhile, 2,6-dichloro-4-tetrazolyl benzoic acid was synthesized by the following methods.

Process 1 Synthesis of 2,6-dichloro-4-methoxycarbonyl benzoic acid methylester
A hexane solution containing 2M trimethylsilyldiazomethane was added to the mixture of 500 mg of 2,6-dichloro-4-carboxybenzoic acid (Maybridge) and 15 ml of methanol until the end point of the reaction. The reaction mixture was concentrated and purified by silica gel chromatography (ethyl acetate/hexane) to obtain the title compound.
Yield: 612 mg
H-NMR (CDCl3) δ 3.95 (3H, s), 4.00 (3H, s), 8.00 (2H, s).

Process 2 Synthesis of 2,6-dichloro-4-carboxybenzoic acid methylester
The mixture of 560 mg of 2,6-dichloro-4-methoxycarbonyl benzoic acid, 85 mg of sodium hydroxide, 5 ml of water and 5 ml of tetrahydrofuran was stirred for 1 hour. The mixture was diluted with 1N hydrochloric acid and treated by an ordinary method using ethyl acetate as an extractant to obtain the title compound.
Yield: 530 mg
H-NMR (CDCl3) δ 4.00 (3H, s), 8.05 (2H, s).

Process 3 Synthesis of 2,6-dichloro-4-carbamolylbenzoic acid methylester
126 μl of ethyl chloroformate was added to the mixture of 300 mg of 2,6-dichloro-4-carboxybenzoic acid methylester, 210 μl of triethylamine and 4 ml of tetrahydrofuran. The produced precipitate was filtered out and 136 mg of (NH4)2CO3 was added to the filtrate and stirred overnight. The obtained substance was treated by an ordinary method using ethyl acetate as an extractant to obtain the title compound.
Yield: 277 mg
H-NMR (CDCl3) δ 4.00 (3H, s), 5.90 (2H, br), 7.75 (2H, s).

Process 4 Synthesis of 2,6-dichloro-4-cyanobenzoic acid methylester
The mixture of 277 mg of 2,6-dichloro-4-carbamolylbenzoic acid methylester, 315 μl of trifluoroacetic anhydride, 542 μl of pyridine and 5 ml of dioxane was stirred overnight. The obtained substance was treated by an ordinary method using ethyl acetate as an extractant and purified by silica gel chromatography (ethyl acetate/hexane) to obtain the title compound.
Yield: 187 mg
H-NMR (CDCl3) δ 4.00 (3H, s), 7.60 (2H, s).

Process 5 Synthesis of 2,6-dichloro-4-tetrazolylbenzoic acid methylester
The mixture of 185 mg of 2,6-dichloro-4-cyanobenzoic acid methylester, 266 mg of azidotributyltin and 5 ml of toluene was stirred at 100° C. for 3 days. The reaction mixture was concentrated and diluted with ethyl acetate. After Celite filtration, the filtrate was concentrated and the residue was purified by reverse phase HPLC to obtain the title compound.
Yield: 110 mg
H-NMR (CDCl3) δ 4.00 (3H, s), 8.15 (2H, s).
MS (ESI, m/z) 271 (M-H).

Process 6 Synthesis of 2,6-dichloro-4-tetrazolylbenzoic acid
The mixture of 110 mg of 2,6-dichloro-4-tetrazolylbenzoic acid methylester, 0.5 ml of dichloromethane solution containing 1M BBr3 and 5 ml of dichloromethane was stirred overnight. The obtained substance was treated by an ordinary method using dichloromethane as an extractant and purified by reverse phase HPLC to obtain the title compound.
Yield: 35 mg
H-NMR (DMSO-d6) δ 8.20 (2H, s).
MS (ESI, m/z) 257 (M-H)—

EXAMPLE 84

The compound of Example 84 in Table 7 was synthesized by the same procedure as shown in Example 83 except that a corresponding carboxylic reagent was used.
Meanwhile, 2,6-dichloro-4-methanesulfonylamino benzoic acid was synthesized by the following methods.

Process 1 Synthesis of 2,6-dichloro-4-(t-butoxycarbonylamino) benzoic acid methylester
The mixture of 150 mg of 2,6-dichloro-4-carboxybenzoic acid methylester, 193 mg of diphenylphospholylazido, 71 mg of triethylamine and 5 ml of t-butanol was stirred at 100° C. for 3 hours. After concentration, the reaction mixture was treated by an ordinary method using ethyl acetate as an extractant and purified by silica gel chromatography (ethyl acetate/hexane) to obtain the title compound.
Yield: 180 mg
H-NMR (CDCl3) δ 1.50 (9H, s), 3.95 (3H, s), 6.65 (1H, s), 7.40 (2H, s).

Process 2 Synthesis of 2,6-dichloro-4-[bis(methanesulfonyl)amino]benzoic acid methylester
10 ml of dioxane solution containing 4N hydrogen chloride was added to 180 mg of 2,6-dichloro-4-(t-butoxycarbonylamino)benzoic acid methylester and stirred for 2 hours. After the solvent was removed, the residue, that is, the mixture of 100 mg of triethylamine, 70 mg of methanesulfonyl chloride and 10 ml of dichloromethane was stirred overnight. The residue obtained by an ordinary method using dichloromethane as an extractant was suspended in a mixed solvent of ethyl acetate-hexane and filtered to obtain the title compound.
Yield: 100 mg
H-NMR (CDCl3) δ 3.40 (6H, s), 4.00 (3H, s), 7.35 (2H, s).

Process 3 Synthesis of 2,6-dichloro-4-methanesulfonylamino benzoic acid methylester
The mixture of 100 mg of 2,6-dichloro-4-[bis(methanesulfonyl)amino]benzoic acid methylester, 3 ml of an aqueous solution of 1N sodium hydroxide and 10 ml of ethanol was stirred. After the solvent was removed, the obtained substance was treated by an ordinary method using ethyl acetate as an extractant to obtain the title compound.
Yield: 60 mg
H-NMR (CDCl3) δ 3.10 (3H, s), 3.95 (3H, s), 7.10 (1H, s), 7.20 (2H, s).

Process 4 Synthesis of 2,6-dichloro-4-methanesulfonylamino benzoic acid
The intended substance was obtained using 100 mg of 2,6-dichloro-4-methanesulfonylamino benzoic acid methylester by the same procedure as that of Process 6 of synthesis of carboxylic acid in Example 83.
Yield: 50 mg
H-NMR (DMSO-d6) δ 3.20 (3H, s), 7.30 (2H, s), 10.40 (1H, s).

EXAMPLE 85

The resin obtained in Process 4 of Example 1 was treated by an ordinary method and the 2-iodobenzoylated resin was prepared. 20 ml of NMP, 2 ml of triethylamine, 1 ml of methyl acrylate, 500 mg of bis(triphenylphosphine) palladium dichloride were added to 100 mg of the obtained resin and stirred at 80° C. for 12 hours. After removing the reaction solvent, the resin was washed with NMP and dichloromethane three times each, and dried under reduced pressure. The resin was treated with trifluoroacetic acid containing 5% of water for 1 hour. After filtration, the resin was concentrated under reduced pressure. The resin was purified by high-pressure liquid chromatography (water/acetonitrile, each containing 0.05%/0.04% trifluoroacetic acid) to obtain 29.3 mg of the compound of Example 85 in Table 7.

EXAMPLES 86 AND 87

The compounds of Examples 86 and 87 were synthesized by the same procedure as shown in Example 85 except that corresponding olefin reagents were used. 17.4 mg of the intended substance was obtained in Example 86 in Table 7 and 22.3 mg of that was obtained in Example 87.

(1-11)

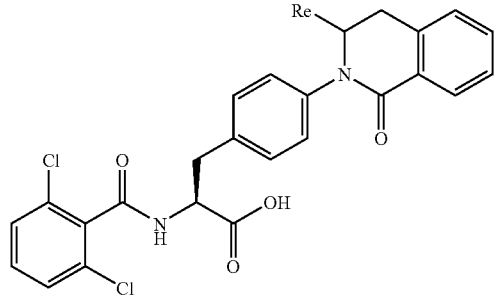

TABLE 7

| Example | Re | MS Found (MH+) |
|---|---|---|
| 85 | Methoxycarbonyl | 541, 543 |
| 86 | Acetyl | 525, 527 |
| 87 | Cyano | 508, 510 |

EXAMPLE 88

VCAM Antagonist Activity (VCAM-1/α 4 β 1 Binding Assay)

The capacity of a test substance antagonistic to the binding of cell strain Jurkat (ATCC TIB-152) of human T cells, known to express integrin α 4 β 1, to VCAM-1 was determined. 100 μl/well of a solution (500 ng/ml) of recombinant human VCAM-1 (R & D systems) solution diluted with buffer A (0.1 M NaHCO$_3$, pH 9.6) was added to a micro titer plate having 96 wells (Nunc Maxisorp). After the incubation at 4° C. overnight, unbound VCAM-1 was removed by washing once with PBS. After completion of the washing, a buffer (buffer B) obtained by diluting Block Ace (Dainippon Pharmaceutical Co., Ltd.) with PBS to 1/4 concentration was added in an amount of 150 μl/well. After the incubation at room temperature for 1 hour, buffer B was removed and the plate was washed with PBS once.

Jurkat cells were washed with Dulbecco modified Eagle medium (SIGMA, hereinafter referred to as "DMEM") twice and then incubated in DMEM containing 10 μg/ml of Calcein-AM (Wako Pure Chemical Industries, Ltd.) at 37° C. in dark place for 30 minutes to label with fluorescence. The cells were again suspended in a binding buffer (20 mM HEPES, DMEM containing 0.1% BSA).

50 μl of a test substance of various concentrations obtained by the dilution with the binding buffer was added to the plate. Immediately thereafter, 50 μl (final volume: 100 μl/well) of the fluorescent Jurkat cells (4×10$^6$ cells/ml) were added thereto, and they were incubated at room temperature for 30 minutes. After the shaking on a plate shaker (IKA MTS-4) at 800 rpm for 30 seconds, the solution was immediately removed to remove the unbound cells. The fluorescence quantity of the bound cells remaining in the wells was determined with a fluorescent plate reader (Wallac 1420 ARVO multi-label counter) (filter excitation wave length: 485 nm, emission wave length: 535 nm). The fluorescent strength thus obtained is proportional to the number of Jurkat cells bound to VCAM-1 and remaining on the plate. The binding rate of each test material in various concentrations was determined while the fluorescent strength of the test material-free well was determined to be 100%. The concentration IC$_{50}$ for the 50% binding inhibition was calculated.

The obtained test results are shown in Table 8.

EXAMPLE 89

VCAM Antagonistic Activity (VCAM-1/α 4 β 7 Binding Assay)

The capacity of a test substance antagonistic to the binding of lymphoma cell strain RPMI-8866 of human B cells, known to express integrin α 4 β 7, to VCAM-1 was determined. 100 μl/well of a solution (500 ng/ml) of recombinant human VCAM-1 (R & D systems) solution diluted with buffer A (0.1 M NaHCO$_3$, pH 9.6) was added to a micro titer plate having 96 wells (Nunc Maxisorp). After the incubation at 4° C. overnight, unbound VCAM-1 was removed by washing once with PBS. After completion of the washing, a buffer (buffer B) obtained by diluting Block Ace (Dainippon Pharmaceutical Co., Ltd.) with PBS to 1/4 concentration was added in an amount of 150 μl/well. After the incubation at room temperature for 1 hour, buffer B was removed and the plate was washed with PBS once.

RPMI-8866 cells were incubated in Dulbecco modified Eagle medium containing 10 μg/ml of Calcein-AM (Wako Pure Chemical Industries, Ltd.) (SIGMA, hereinafter referred to as "DMEM") at 37° C. for 30 minutes to label with fluorescence. The cells were again suspended in a binding buffer (20 mM HEPES, DMEM containing 0.1% BSA) containing 4 mM of MnCl$_2$.

50 μl of a test substance of various concentrations obtained by the dilution with the binding buffer was added to the plate. Immediately thereafter, 50 μl (final volume: 100 μl/well) of the fluorescent RPMI-8866 cells (4×10$^6$ cells/ml) were added thereto, and they were incubated at room temperature for 30 minutes. After the shaking on a plate shaker (IKA MTS-4) at 800 rpm for 30 seconds, the solution was immediately removed to remove the unbound cells. The fluorescence quantity of the bound cells remaining in the wells was determined with a fluorescent plate reader (Wallac 1420 ARVO multi-label counter) (filter excitation wave length: 485 nm, emission wave length: 535 nm). The fluorescent strength thus obtained is proportional to the number of RPMI-8866 cells bound to VCAM-1 and remaining on the plate. The binding rate of each test material in various concentrations was determined while the fluorescent strength of the test material-free well was determined to be 100%. The concentration $IC_{50}$ for the 50% binding inhibition was calculated.

The obtained test results are shown in Table 8.

TABLE 8

| | Antagonistic Activity IC50 (μM) | |
|---|---|---|
| Example No. | α 4 β 1/VCAM | α 4 β 7/VCAM |
| 1 | 0.21 | 0.0097 |
| 2 | 0.14 | 0.008 |
| 3 | 0.33 | 0.0085 |
| 4 | 0.5 | 0.02 |
| 6 | 0.24 | 0.011 |
| 7 | 0.27 | 0.018 |
| 9 | 0.77 | 0.024 |
| 15 | 0.74 | 0.034 |
| 16 | 1.1 | 0.027 |
| 17 | 1.9 | 0.14 |
| 25 | 5 | 0.16 |
| 26 | 5.3 | 0.08 |
| 27 | 2.8 | 0.073 |
| 29 | 0.6 | 0.023 |
| 30 | 0.45 | 0.046 |
| 33 | 0.26 | 0.0089 |
| 36 | 0.033 | 0.0026 |
| 37 | 0.14 | 0.0058 |
| 38 | 0.22 | 0.013 |
| 40 | 0.24 | 0.018 |
| 41 | 0.63 | 0.019 |
| 42 | 0.56 | 0.021 |
| 43 | 1.6 | 0.043 |
| 44 | 1.4 | 0.039 |
| 45 | 1.2 | 0.019 |
| 46 | 1.7 | 0.042 |
| 47 | 2.1 | 0.092 |
| 48 | 1.3 | 0.021 |
| 49 | 2 | 0.06 |
| 59 | 0.073 | 0.01 |
| 71 | 0.41 | 0.23 |
| 72 | 0.15 | 0.0045 |
| 73 | 0.21 | 0.0085 |
| 74 | 1.2 | 0.11 |
| 75 | 0.79 | 0.055 |
| 76 | 1.2 | 0.096 |
| 77 | 0.77 | 0.073 |
| 78 | 0.52 | 0.042 |
| 79 | 0.57 | 0.086 |
| 80 | 1.1 | 0.080 |
| 81 | 0.58 | 0.044 |
| 82 | 3.50 | 0.90 |
| 83 | 0.0059 | 0.00055 |
| 84 | 0.015 | 0.0006 |
| 85 | 1.10 | 0.084 |
| 86 | 0.53 | 0.039 |
| 87 | 0.77 | 0.084 |

It is thus apparent that the new phenylalanine derivatives exhibited an excellent α 4-integrin inhibiting activity.

Since the new phenylalanine derivatives of the present invention have excellent α 4-integrin inhibiting activity, the present invention provides a therapeutic agent or preventive agent for diseases in which α4 integrin-depending adhesion process participates in the pathology, such as inflammatory diseases, rheumatoid arthritis, inflammatory bowel diseases, systemic lupus erythematosus, multiple sclerosis, Sjögren's syndrome, asthma, psoriasis, allergy, diabetes, cardiovascular diseases, arterial sclerosis, restenosis, tumor proliferation, tumor metastasis and transplantation rejection. The above-described inflammatory bowel diseases include Crohn's disease and ulcerative colitis.

The compound of the present invention has high bioavailability or blood level when administered orally. Therefore, an oral administration of a drug is effective.

The compound of the present invention also has high stability in acidic or alkaline solution and for example, it is possible to apply to various dosage forms.

What is claimed is:

1. A phenylalanine compound of formula (1) or a pharmaceutically acceptable salt thereof:

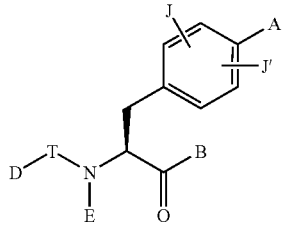

(1)

wherein A represents one of formula 24, 25-1, 25-3, 25-4, or 26-1

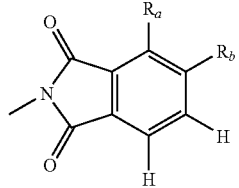

(24)

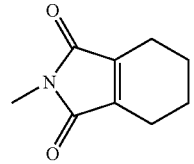

(25-1)

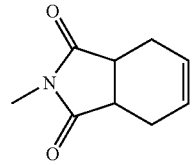

(25-3)

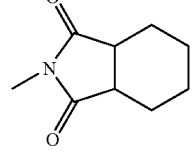

(25-4)

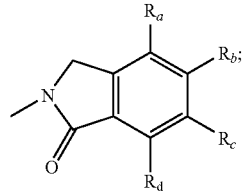

(26-1)

E represents a hydrogen atom;
T represents a C=(O) group;
D represents an aryl group;
B represents a hydroxyl group or lower alkoxyl group;
J and J' may be the same or different from each other and each represents a hydrogen atom, a halogen atom, a lower alkyl group, a lower alkyloxy group or nitro group
wherein in formula 24
Ra represents a hydrogen atom, a fluorine atom, a chloro atom, a bromo atom, a nitro group, an alkyl group having 1 to 3 carbon atoms or an alkoxyl group having 1 to 3 carbon atoms,
Rb represents a hydrogen atom, a fluorine atom, a chloro atom, a bromo atom, a nitro group, an alkyl group having 1 to 3 carbon atoms, an amino group, an amino group substituted by one or two alkyl groups having 1 to 3 carbon atoms, a carbamoyl group or a carbamoyl group substituted by one or two alkyl groups having 1 to 3 carbon atoms; and
in formula 26-1
Ra to Rd may be the same or different from each other, and each represents a hydrogen atom, a halogen atom, a hydroxyl group, a lower alkyl group which may contain a hetero atom(s) in the chain thereof, a lower alkenyl group which may contain a hetero atom(s) in the chain thereof, a lower alkynyl group which may contain a hetero atom(s) in the chain thereof, a cycloalkyl group which may contain a hetero atom(s) in the ring thereof, an aryl group, a heteroaryl group, a lower alkyl group substituted with a cycloalkyl group(s) which may contain a hetero atom(s) in the ring thereof, a lower alkyl group substituted with an aryl group(s), a lower alkyl group substituted with a heteroaryl group(s), a lower alkoxyl group, a lower alkoxyl group substituted with a cycloalkyl group(s) which may contain a hetero atom(s) in the ring thereof, a lower alkoxyl group substituted with an aryl group(s), a lower alkoxyl group substituted with a heteroaryl group(s), a cycloalkyloxy group which may contain a hetero atom(s) in the ring thereof, an aryloxy group, a heteroaryloxy group, a lower hydroxyalkyl group, a lower hydroxyalkenyl group, a lower hydroxylalkoxyl group, a lower halogenoalkyl group, a lower halogenoalkoxyl group, a lower halogenoalkenyl group, nitro group, cyano group, a substituted or unsubstituted amino group, carboxyl group, a lower alkyloxycarbonyl group, a substituted or unsubstituted carbamoyl group, a lower alkanoyl group, an aroyl group, a lower alkylthio group, a lower alkylsulfonyl group, a substituted or unsubstituted sulfonylamino group or a substituted or unsubstituted sulfamoyl group, and Ra, Rb, Rc and Rd may form a ring between them.

2. The phenylalanine compound or pharmaceutically acceptable salt thereof according to claim 1, wherein A represents the formula (24):

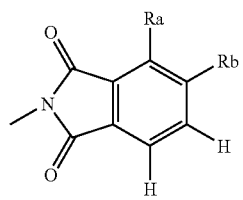

(24)

and

J and J' represent a hydrogen atom.

3. The phenylalanine compound or pharmaceutically acceptable salt thereof according to claim 2, wherein D represents 2,6-dichlorophenyl group, 2,6-dichloro-4-tetrazolylphenyl group, 2,6-dichloro-4-lower-alkylsulfonylaminophenyl group or 3,5-dichloropyridine-4-yl group.

4. The phenylalanine compound or pharmaceutically acceptable salt thereof according to claim 1, wherein A represents formula (25-1), (25-3) or (25-4):

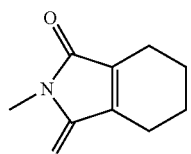

(25-1)

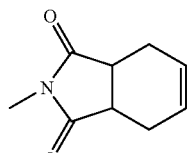

(25-3)

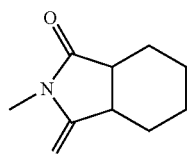

(25-4)

and

J and J' represent a hydrogen atom.

5. The phenylalanine compound or pharmaceutically acceptable salt thereof according to claim 4, wherein D represents 2,6-dichlorophenyl group, 2,6-dichloro-4-tetrazolylphenyl group, 2,6-dichloro-4-lower-alkylsulfonylaminophenyl group or 3,5-dichloropyridine-4-yl group.

6. The phenylalanine compound or pharmaceutically acceptable salt thereof according to claim 1, wherein A represents formula (26-1):

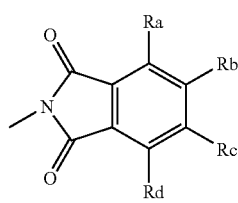

(26-1)

and

J and J' represent a hydrogen atom.

7. The phenylalanine compound or pharmaceutically acceptable salt thereof according to claim 6, wherein D represents 2,6-dichlorophenyl group, 2,6-dichloro-4-tetrazolylphenyl group, 2,6-dichloro-4-lower-alkylsulfonylaminophenyl group or 3,5-dichloropyridine-4-yl group.

8. The phenylalanine compound or pharmaceutically acceptable salt thereof according to claim 1, represented by:

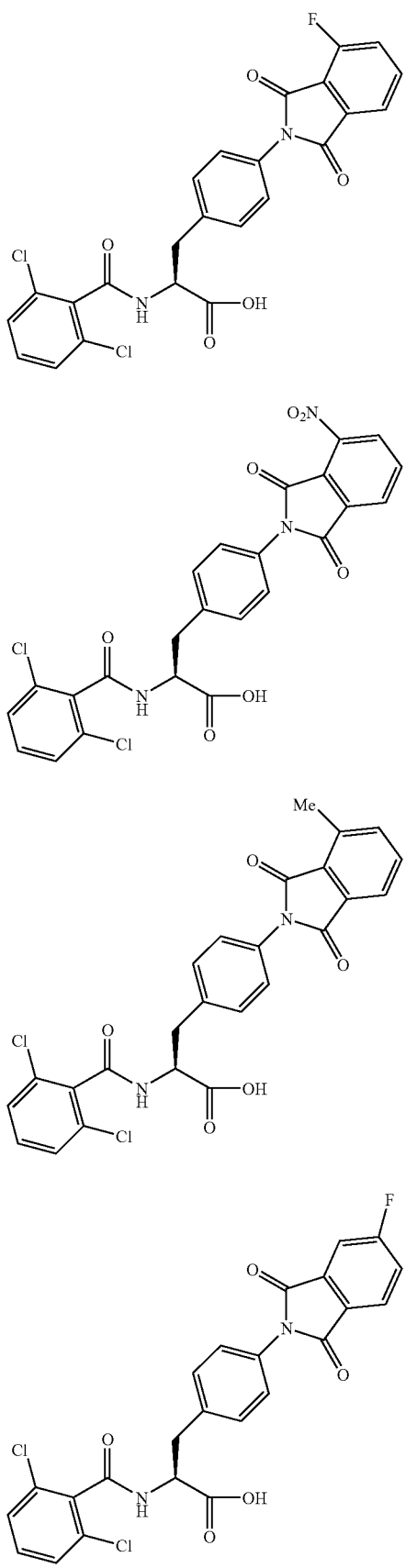
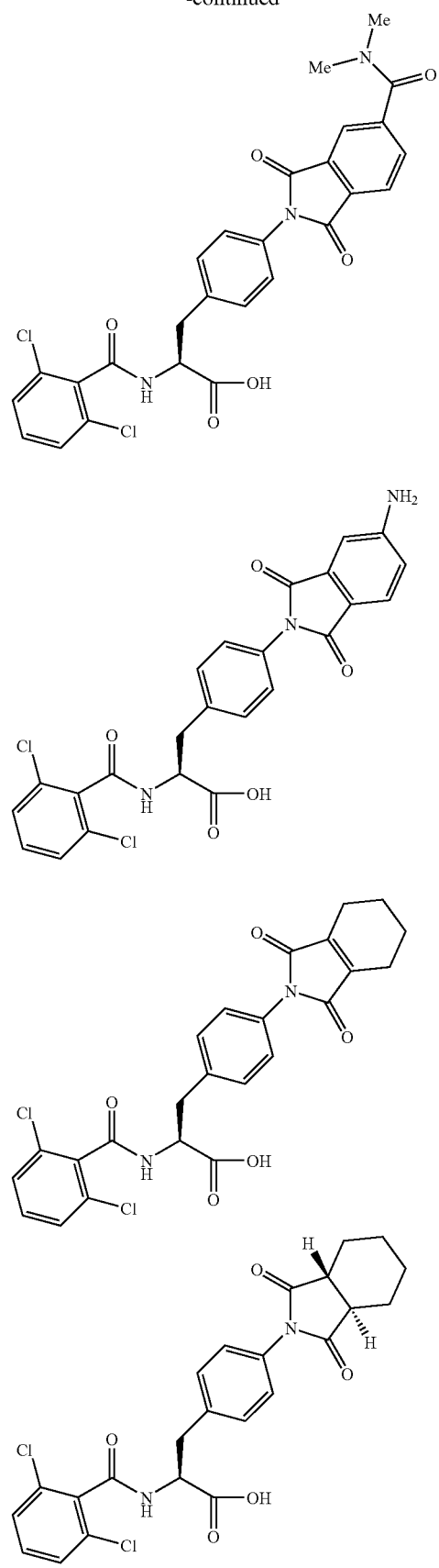

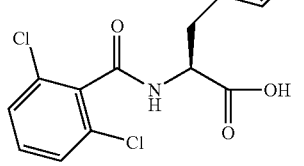
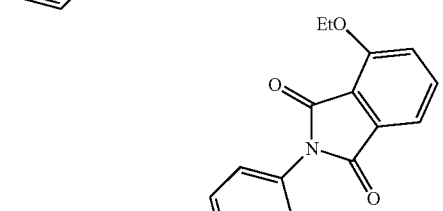
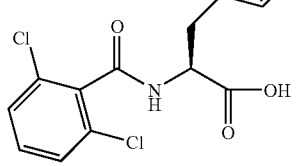
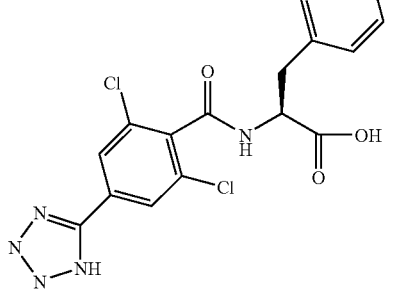
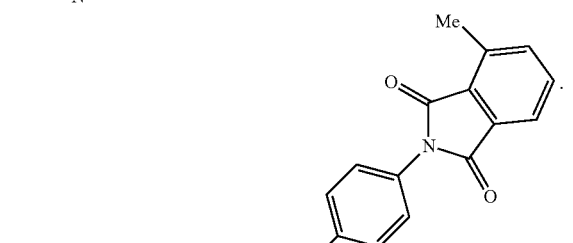
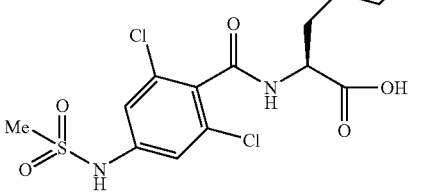

9. A method of treating inflammatory diseases in which an α 4 integrin-depending adhesion process participates in the pathology, which comprises administering a therapeutically effective amount of a phenylalanine compound or a pharmaceutically acceptable salt thereof according to claim 1 to a subject in need thereof.

10. A method of treating rheumatoid arthritis, inflammatory bowel diseases, systemic lupus erythematosus, multiple sclerosis, Sjägren's syndrome, asthma, psoriasis, allergy, arterial sclerosis, and restenosis, which comprises administering a therapeutically effective amount of a phenylalanine compound or a pharmaceutically acceptable salt thereof according to claim 1 to a subject in need thereof.

11. A composition comprising a phenylalanine compound or a pharmaceutically acceptable salt thereof according to claim 1 and a pharmaceutically acceptable carrier.

12. The composition according to claim 11, wherein A represents formula 24, and D represents an aryl group.

13. The composition according to claim 11, wherein A represents formula 24.

14. The composition according to claim 11, wherein A represents formula 25-1, and D represents an aryl group.

15. The composition according to claim 11, wherein A represents formula 25-1.

16. The composition according to claim 11, wherein A represents formula 25-3, and D represents an aryl group.

17. The composition according to claim 11, wherein A represents formula 25-3.

18. The composition according to claim 11, wherein A represents formula 25-4, and D represents an aryl group.

19. The composition according to claim 11, wherein A represents formula 25-4.

20. The composition according to claim 11, wherein A represents formula 26-1, and D represents an aryl group.

21. The composition according to claim 11, wherein A represents formula 26-1.

22. The compound according to claim 1, wherein A represents formula 24.

23. The compound according to claim 1, wherein A represents formula 25-1.

24. The compound according to claim 1, wherein A represents formula 25-3.

25. The compound according to claim 1, wherein A represents formula 25-4.

26. The compound according to claim 1, wherein A represents formula 26-1.

* * * * *